US011744866B2

(12) United States Patent
Hazan

(10) Patent No.: US 11,744,866 B2
(45) Date of Patent: Sep. 5, 2023

(54) METHODS OF PREVENTING AND TREATING COVID-19 INFECTION WITH PROBIOTICS

(71) Applicant: Sabine Hazan, Ventura, CA (US)

(72) Inventor: Sabine Hazan, Ventura, CA (US)

( * ) Notice: Subject to any disclaimer, the term of this patent is extended or adjusted under 35 U.S.C. 154(b) by 0 days.

(21) Appl. No.: 17/200,585

(22) Filed: Mar. 12, 2021

(65) Prior Publication Data

US 2021/0290697 A1     Sep. 23, 2021

Related U.S. Application Data

(63) Continuation-in-part of application No. 17/026,051, filed on Sep. 18, 2020, now Pat. No. 11,253,534.

(60) Provisional application No. 63/002,486, filed on Mar. 31, 2020, provisional application No. 62/991,699, filed on Mar. 19, 2020, provisional application No. 62/991,146, filed on Mar. 18, 2020, provisional application No. 62/991,190, filed on Mar. 18, 2020.

(51) Int. Cl.
| | |
|---|---|
| *A61K 35/745* | (2015.01) |
| *A61K 35/742* | (2015.01) |
| *A61K 35/741* | (2015.01) |
| *A61K 38/14* | (2006.01) |
| *C12Q 1/70* | (2006.01) |
| *A61K 31/439* | (2006.01) |
| *A61K 31/7048* | (2006.01) |
| *A61K 35/24* | (2015.01) |
| *A61P 31/14* | (2006.01) |
| *A61K 31/65* | (2006.01) |
| *A61K 35/74* | (2015.01) |

(52) U.S. Cl.
CPC .......... *A61K 35/745* (2013.01); *A61K 31/439* (2013.01); *A61K 31/65* (2013.01); *A61K 31/7048* (2013.01); *A61K 35/24* (2013.01); *A61K 35/74* (2013.01); *A61K 35/741* (2013.01); *A61K 35/742* (2013.01); *A61K 38/14* (2013.01); *A61P 31/14* (2018.01); *C12Q 1/70* (2013.01)

(58) Field of Classification Search
None
See application file for complete search history.

(56) References Cited

U.S. PATENT DOCUMENTS

| | | | |
|---|---|---|---|
| 3,482,082 A | 12/1969 | Isreeli et al. | |
| 7,026,360 B1 | 4/2006 | Festo | |
| 7,351,739 B2 | 4/2008 | Ho et al. | |
| 8,178,516 B2 | 5/2012 | Shapiro | |
| 10,434,116 B2 | 10/2019 | Frieman et al. | |
| 10,561,690 B2 * | 2/2020 | Borody | A61P 1/04 |
| 10,987,329 B1 | 4/2021 | Raju et al. | |
| 11,077,052 B1 * | 8/2021 | Reddy | A61K 35/741 |
| 11,166,971 B2 | 11/2021 | Hazan | |
| 11,253,534 B2 | 2/2022 | Hazan | |
| 11,278,520 B2 | 3/2022 | Hazan | |
| 2002/0155519 A1 | 10/2002 | Lindner et al. | |
| 2004/0071757 A1 | 4/2004 | Rolf | |
| 2005/0245502 A1 | 11/2005 | Keller | |
| 2006/0189542 A1 | 8/2006 | Furukawa et al. | |
| 2006/0241059 A1 | 10/2006 | Keller | |
| 2007/0026056 A1 | 2/2007 | Rolf | |
| 2007/0031510 A1 | 2/2007 | Flavin-Koenig | |
| 2007/0260204 A1 | 11/2007 | Akagi et al. | |
| 2009/0075311 A1 | 3/2009 | Karl | |
| 2012/0077786 A1 | 3/2012 | Byron et al. | |
| 2012/0252012 A1 | 10/2012 | Armougom et al. | |
| 2014/0017720 A1 | 1/2014 | Sidorsky et al. | |
| 2014/0086877 A1 | 3/2014 | Hlavka | |
| 2014/0147501 A1 | 5/2014 | Van Lengerich | |
| 2014/0349969 A1 | 11/2014 | Penninger et al. | |
| 2015/0309021 A1 | 10/2015 | Birnbaum et al. | |
| 2016/0015786 A1 | 1/2016 | Levesque et al. | |
| 2016/0095850 A1 | 4/2016 | Cooper et al. | |
| 2017/0189443 A1 | 7/2017 | Parsons et al. | |
| 2017/0239303 A1 | 8/2017 | Jones et al. | |
| 2017/0246214 A1 | 8/2017 | Sadowsky et al. | |
| 2017/0360848 A1 | 12/2017 | Adams et al. | |
| 2018/0153944 A1 | 6/2018 | Knights et al. | |
| 2019/0085069 A1 | 3/2019 | Giles-Komar et al. | |
| 2020/0085737 A1 | 3/2020 | Bellinger et al. | |
| 2020/0102287 A1 | 4/2020 | Page et al. | |
| 2020/0172480 A1 | 6/2020 | Zhao et al. | |
| 2020/0237689 A1 | 7/2020 | Peralta et al. | |
| 2021/0290697 A1 | 9/2021 | Hazan | |

(Continued)

FOREIGN PATENT DOCUMENTS

| | | |
|---|---|---|
| CA | 1160570 | 1/1984 |
| EP | 3513782 | 7/2019 |

(Continued)

OTHER PUBLICATIONS

Ianiro et al. "Screening of faecal microbiota transplant donors during the COVID-19 outbreak: suggestions for urgent updates from an international expert panel". Lancet, 2020 vol. 5, pp. 430-432; published on line Mar. 16, 2020.*
Aparstin et al. Clinics and Research in Hepatology and Gastroenterology, 2020, 44, pp. e113-e114 (available online Sep. 4, 2020).*
Sokol et al. PNAS. 2008, vol. 105, No. 43, pp. 16731-16736.*
Yun Kit Yeoh et al. Gut 2021, 70, pp. 698-706.*

(Continued)

*Primary Examiner* — Vera Afremova

(74) *Attorney, Agent, or Firm* — Cislo & Thomas, LLP

(57) ABSTRACT

Methods of preventing and treating COVID-19 infection by administering probiotics. The probiotics can be administered via the following methods: fecal transplant, suppository, or orally. The probiotic contains one or more of the following microorganisms: *Bifidobacterium, Clostridium, Veillonella, Ruminococcus*, and *Sutterella*.

17 Claims, 5 Drawing Sheets

(56) References Cited

U.S. PATENT DOCUMENTS

| | | |
|---|---|---|
| 2021/0290718 A1 | 9/2021 | Hazan |
| 2021/0308167 A1 | 10/2021 | Hazan |

FOREIGN PATENT DOCUMENTS

| | | |
|---|---|---|
| JP | 2014042514 | 3/2014 |
| WO | WO0078268 | 12/2000 |
| WO | WO2007023370 | 3/2007 |
| WO | WO2011084662 | 7/2011 |
| WO | WO2013040526 | 3/2013 |
| WO | WO2014138999 | 9/2014 |
| WO | WO2016164402 | 10/2016 |
| WO | WO2018017880 | 1/2018 |
| WO | WO2018085817 | 5/2018 |
| WO | WO2018161039 | 9/2018 |
| WO | WO2019014714 | 1/2019 |
| WO | WO2019051380 | 3/2019 |
| WO | WO2019197836 | 10/2019 |
| WO | WO2019199918 | 10/2019 |
| WO | WO2020051498 | 3/2020 |
| WO | WO2020214716 | 10/2020 |

OTHER PUBLICATIONS

Kearns et al. "Large, single-dose, oral vitamin D supplementation in adult populations: A systematic review", Endocr Pract. Apr. 2014; 20 (4); 341-351.

De Vuyst L, Moens F, Selak M, Riviere A, Leroy F. Summer Meeting 2013: growth and physiology of bifidobacteria. J Appi Microbiol. 2014;116(3):477-491, https://sfamjournals.onlinelibrary.wiley.com/doi/10.1111/jam.12415, Published 2013.

Parameswaran N, Patiai S. Tumor necrosis factor-alpha signaling in macrophages. Crit Rev Eukaryot Gene Expr. 2010;20(2):87-103, https://www.ncbi.nlm.nih.gov/pmc/articles/PMC3066460/pdf/nihms281055.pdf, Published 2010.

Marras L, Caputo M, Bisicchia S, et al. The Role of Bifidobacteria in Predictive and Preventive Medicine: A Focus on Eczema and Hypercholesterolemia. Microorganisms. 2021:9(4), https://www.ncbi.nlm.nih.gov/pmc/articles/PMC8070932/pdf/microorganisms-09-00836.pdf, Published 2021.

Stavropoulou E, Bezirtzoglou E. Probiotics in medicine: A long debate. Front Immunol. 2020;11:2192-2192, https://www.ncbi.nlm.nih.gov/pmc/articles/PMC7544950/pdf/fimmu-11-02192.pdf, Published Sep. 25, 2020.

Martins AKS, Martins FS, Gomes DA, et al. Evaluation of in vitro antagonism and of in vivo immune modulation and protection against pathogenic experimental challenge of two probiotic strains of Bifidobacterium animalis var. lactis. Arch Microbiol. 2010;192(12):995-1003, Published Sep. 17, 2010.

Ruiz L, Delgado S, Ruas-Madiedo P, Sanchez B, Margolles A. Bifidobacteria and their molecular communication with the immune system. Front Microbiol. 2017;8:2345-2345, https://www.frontiersin.org/articles/10.3389/fmicb.2017.02345/full, Published Dec. 4, 2017.

Arboleya S, Watkins C, Stanton C, Ross RP. Gut. Bifidobacteria Populations in Human Health and Aging. Front Microbiol. 2016;7:1204, Published Aug. 19, 2016.

Ahlawat S, Asha, Sharma KK. Immunological co-ordination between gut and lungs in SARS-CoV-2 infection. Virus Res, 2020;286:198103-198103, https://www.ncbi.nlm.nih.gov/pmc/articles/PMC7380259/pdf/main.pdf, Published Jul. 24, 2020.

Follmer C. Viral infection-induced gut dysbiosis, neuroinflammation, and α-synuclein aggregation: Updates and perspectives on COVID-19 and neurodegenerative disorders. ACS chemical neuroscience. 2020;11(24):4012-4016, Published Nov. 27, 2020.

Marsland BJ, Trompette A, Gollwitzer ES. The Gut-Lung Axis in Respiratory Disease. Ann Am Thorac Soc. 2015;12 Suppl 2:S150-156, https://www.atsjournals.org/doi/pdf/10.1513/AnnalsATS.201503-133AW, Published 2015.

Gu S, Chen Y, Wu Z, et al. Alterations of the Gut Microbiota in Patients With Coronavirus Disease 2019 or H1N1 Influenza. Clin Infect Dis. 2020;71(10):2669-2678, https://www.ncbi.nlm.nih.gov/pmc/articles/PMC7314193/pdf/ciaa709.pdf, Published 2020.

Zuo T, Liu Q, Zhang F, et al. Depicting SARS-CoV-2 faecal viral activity in association with gut microbiota composition in patients with COVID-19. Gut. 2021;70(2):276-284, https://www.ncbi.nlm.nih.gov/pmc/articles/PMC7385744/pdf/gutjnl-2020-322294.pdf, Published Jul. 20, 2020.

Yeoh YK, Zuo T, Lui GC, et al. Gut microbiota composition reflects disease severity and dysfunctional immune responses in patients with COVID-19. Gut. 2021;70(4):698-706, https://www.ncbi.nlm.nih.gov/pmc/articles/PMC7804842/pdf/gutjni-2020-323020.pdf, Published Jan. 11, 2021.

Xu K, Cai H, Shen Y, et al. [Management of COVID-19: the Zhejiang experience], Zhejiang Da Xue Xue Bao Yi Xue Ban. 2020;49(2):147-157, http://www.zjujournals.com/med/CN/10.3785/j.issn.1008-9292.2020.02.02, Published Apr. 2020.

Din AU, Hassan A, Zhu Y, et al. Inhibitory effect of Bifidobacterium bifidum ATCC 29521 on colitis and its mechanism. J Nutr Biochem. 2020;79:108353, Published 2020.

Nitzan O, Elias M, Peretz A, Saiiba W. Role of antibiotics for treatment, of inflammatory bowel disease. World J Gastroenterol. 2016;22(3):1078-1087, https://www.ncbi.nlm.nih.gov/pmc/articles/PMC4716021/pdf/WJG-22-1078.pdf, Published Jan. 21, 2016.

Valdes-Varela L, Hernandez-Barranco AM, Ruas-Madiedo P, Gueimonde M. Effect of Bifidobacterium upon Clostridium difficile Growth and Toxicity When Co-cultured in Different Prebiotic Substrates. Front Microbiol. 2016;7:738, Published May 18, 2016.

Wei Y, Yang F, Wu Q, et al. Protective effects of Bifidobacterial strains against toxigenic Clostridium difficile. Front Microbiol. 2018;9:888-888, https://www.frontiersin.org/articles/10.3389/fmicb.2016.00738/full, Published May 8, 2018.

Philippe D, Heupel E, Bium-Sperisen S, Riedel CU. Treatment with Bifidobacterium bifidum 17 partially protects mice from Th1-driven inflammation in a chemically induced model of colitis. Int J Food Microbiol. 2011;149(1):45-49, Published Dec. 31, 2010.

Groeger D, Schiavi E, Grant R, et al. Intranasal Bifidobacterium iongum protects against viral-induced lung inflammation and injury in a murine model of lethal influenza infection. EBioMedicine. 2020,60:102981, https://www.ncbi.nlm.nih.gov/pmc/articles/PMC7495089/pdf/main.pdf, Published 2020.

Janda L, Mihalcin M, Stastna M. is a healthy microbiome responsible for lower mortality in COVID-19? Biologia (Bratisl). 2020:1-11, https://link.springer.com/conten/pdf/10.2478/s11756-020-00614-8.pdf, Oct. 15, 2020.

Tiwari SK, Dicks LMT, Popov IV, et al. Probiotics at War Against Viruses: What Is Missing From the Picture? Front Microbiol. 2020;11:1877, https://www.frontiersin.org/articles/10.3389/fmicb.2020.01877/full, Published Aug. 20, 2020.

Bozkurt HS, Quigley EM. The probiotic Bifidobacterium in the management of Coronavirus: A theoretical basis. Int J Immunopathol Pharmacol. 2020;34:2058738420961304, https://www.ncbi.nlm.nih.gov/pmc/articles/PMC7786419/pdf/10.1177_2058738420961304.pdf, Published Sep. 2, 2020.

Jin X, Lian JS, Hu JH, et al. Epidemiological, clinical and virological characteristics of 74 cases of coronavirus-infected disease 2019 (COVID-19) with gastrointestinal symptoms. Gut. 2020;69(6):1002-1009, https://www.ncbi.nlm.nih.gov/pmc/articles/PMC7133387/pdf/gutjnl-2020-320926.pdf, Published Mar. 24, 2020.

Tao W, Zhang G, Wang X, et al. Analysis of the intestinal microbiota in COVID-19 patients and its correlation with the inflammatory factor IL-18. Med Microecol. 2020;5:100023, https://reader.elsevier.com/reader/sd/pii/S2590097820300203?token=6B154F1B7E5EE1BE55F3B9AA9D50570D1CD4D2F1092710CB2CB0347C67241BB09E54F85E307B730A69D212B98B7DFDB0&originRegion=us-east-1&originCreation=20210927181504, Published Sep. 28, 2020.

Kostic AD, Xavier RJ, Gevers D. The microbiome in inflammatory bowel disease: current status and the future ahead. Gastroenterology. 2014:146(6):1489-1499, https://www.ncbi.nlm.nih.gov/pmc/articles/PMC4034132/pdf/nihms580479.pdf, Published 2014.

Tian Y, Rong L, Nian W, He Y, Review article: gastrointestinal features in COVID-19 and the possibility of faecal transmission. Aliment Pharmacol Ther. 2020;51(9):843-851, https://www.ncbi.nlm.nih.gov/pmc/articles/PMC7161803/pdf/APT-51-843.pdf, Published 2020.

(56) References Cited

OTHER PUBLICATIONS

Zhao M. Cytokine storm and immunomodulatory therapy in COVID-19: Role of chloroquine and anti-IL-6 monoclonal antibodies. Int J Antimicrob Agents. 2020;55(6):105982, https://www.ncbi.nlm.nih.gov/pmc/articles/PMC7161506/pdf/main.pdf, Published 2020.

Liang W, Feng Z, Rao S, et al. Diarrhoea may be underestimated: a missing link in 2019 novel coronavirus. Gut. 2020;69(6):1141-1143, https://gut.bmj.com/content/gutjnl/69/6/1141.full.pdf. Published Feb. 26, 2020.

Negi S, Das DK, Pahari S, Nadeem S, Agrewala JN. Potential role of gut microbiota in induction and regulation of innate immune memory. Front Immunol. 2019;10(2441), https://www.frontiersin.org/articles/10.3389/fimmu.2019.02441/full, Published Oct. 25, 2019.

Lloyd-Price J, Abu-Ali G, Huttenhower C. The healthy human microbiome. Genome Med. 2016;8(1):51, https://genomemedicine.biomedcentral.com/track/pdf/10.1186/s13073-016-0307-y.pdf, Published 2016.

Ghouri YA, Richards DM, Rahimi EF, Krill JT, Jelinek KA, DuPont AW. Systematic review of randomized controlled trials of probiotics, prebiotics, and synbiotics in inflammatory bowel disease. Clin Exp Gastroenterol. 2014;7:473-487, https://www.ncbi.nlm.nih.gov/pmc/articles/PMC4266241/pdf/ceg-7-473.pdf, Published 2014.

Fanning S, Hall LJ, Cronin M, et al. Bifidobacterial surface-exopolysaccharide facilitates commensal-host interaction through immune modulation and pathogen protection. Proc Natl Acad Sci U S A. 2012;109(6):2108-2113, https://www.pnas.org/content/pnas/109/6/2108.full.pdf, Published Feb. 7, 2012.

Hughes KR, Harnisch LC, Alcon-Giner C, et al. Bifidobacterium breve reduces apoptotic epithelial cell shedding in an exopolysaccharide and MyD88-dependent manner. Open Biol. 2017;7(1), https://www.ncbi.nlm.nih.gov/pmc/articles/PMC5303268/pdf/rsob-7-160155.pdf, Published 2017.

Ferreira-Halder CV, Faria AVS, Andrade SS. Action and function of Faecalibacterium prausnitzii in health and disease. Best Pract Res Clin Gastroenterol. 2017;31(6):643-648, Published 2017.

Ganesan K, Chung SK, Vanamala J, Xu B. Causal Relationship between Diet-Induced Gut Microbiota Changes and Diabetes: A Novel Strategy to Transplant Faecalibacterium prausnitzii in Preventing Diabetes. Int J Mol Sci. 2018:19(12), https://www.ncbi.nlm.nih.gov/pmc/articles/PMC6320976/pdf/ijms-19-03720.pdf, Published Nov. 22, 2018.

Greene MW, Roberts AP, Fruge AD. Negative Association Between Mediterranean Diet Adherence and COVID-19 Cases and Related Deaths in Spain and 23 OECD Countries: An Ecological Study. Front Nutr. 2021 8:591964, https://www.ncbi.nlm.nih.gov/pmc/articles/PMC7973012/pdf/fnut-08-591964.pdf, Published Mar. 5, 2021.

Arboleya S. Watkins C. Stanton C, Ross RP. Gut Bifidobacteria popuiations in human health and aging. Front Microbiol. 2016;7(1204), https://www.frontiersin.org/articles/10.3389/fmicb.2016.01204/full, Aug. 19, 2016.

Tang L, Yin Z, Hu Y, Mei H. Controlling Cytokine Storm Is Vital in COVID-19. Front Immunol. 2020;11:570993, https://www.frontiersin.org/articles/10.3389/fimmu.2020.570993/full, Published Nov. 30, 2020.

Ferreira C, Viana SD, Reis F. Gut Microbiota Dysbiosis-Immune Hyperresponse-Inflammation Triad in Coronavirus Disease 2019 (COVID-19): Impact of Pharmacological and Nutraceutical Approaches. Microorganisms 2020; 8(10). Oct. 2020.

Yeoh YK, Zuo T, Lui GC, et al. Gut microbiota composition reflects disease severity and dysfunctional immune responses in patients with COVID-19. Gut 2021. Jan. 2021.

Zhou F, Yu T, Du R, et al. Clinical course and risk factors for mortality of adult inpatients with COVID-19 in Wuhan, China: a retrospective cohort study. Lancet 2020; 395(10229): 1054-62. Mar. 2020.

Gasbarrini G, Dionisi T, Franceschi F, Gasbarrini A. Editorial—COVID-19 and the microbiota: new kids on the block. Eur Rev Med Pharmacol Sci 2020; 24(9): 5189-91. Jan. 2020.

Janda L, Mihalcin M, Stastna M. Is a healthy microbiome responsible for lower mortality in COVID-19? Biologia (Bratisl) 2020: 1-11. Oct. 2020.

Galeotti C, Bayry J. Autoimmune and inflammatory diseases following COVID-19. Nat Rev Rheumatol 2020; 16(8): 413-4. Jun. 2020.

Tay MZ, Poh CM, Renia L, MacAry PA, Ng LFP. The trinity of COVID-19: immunity, inflammation and intervention. Nat Rev Immunol 2020; 20(6): 363-74. Apr. 2020.

Zuo T, Zhang F, Lui GCY, et al. Alterations in Gut Microbiota of Patients With COVID-19 During Time of Hospitalization. Gastroenterology 2020; 159(3): 944-55 e8. May 2020.

Ferreira C, Viana SD, Reis F. Is Gut Microbiota Dysbiosis a Predictor of Increased Susceptibility to Poor Outcome of COVID-19 Patients? An Update. Microorganisms 2020; 9(1). Dec. 2020.

Follmer C. Gut Microbiome Imbalance and Neuroinflammation: Impact of COVID-19 on Parkinson's Disease. Mov Disord 2020; 35(9): 1495-6. Aug. 2020.

Belancic A. Gut microbiome dysbiosis and endotoxemia—Additional pathophysiological explanation for increased COVID-19 severity in obesity. Obes Med 2020; 20: 100302. Sep. 2020.

Follmer C. Viral Infection-Induced Gut Dysbiosis, Neuroinflammation, and alpha-Synuclein Aggregation: Updates and Perspectives on COVID-19 and Neurodegenerative Disorders. ACS Chem Neurosci 2020; 11(24): 4012-6. Nov. 2020.

Zuo T, Zhan H, Zhang F, et al. Alterations in Fecal Fungal Microbiome of Patients With COVID-19 During Time of Hospitalization until Discharge. Gastroenterology 2020; 159(4): 1302-10 e5. Jun. 2020.

Kim HS. Do an Altered Gut Microbiota and an Associated Leaky Gut Affect COVID-19 Severity? mBio 2021; 12(1). Jan. 2021.

Gohil K, Samson R, Dastager S, Dharne M. Probiotics in the prophylaxis of COVID-19: something is better than nothing. 3 Biotech 2021; 11(1): Nov. 1, 2020.

Ahlawat S, Asha, Sharma KK. Immunological co-ordination between gut and lungs in SARS-CoV-2 infection. Virus Res 2020; 286: 198103. Jul. 2020.

Marsland BJ, Trompette A, Gollwitzer ES. The Gut-Lung Axis in Respiratory Disease. Ann Am Thorac Soc 2015; 12 Suppl 2:S150-6. May 2015.

Antunes Aec, Vinderola G, Xavier-Santos D, Sivieri K. Potential contribution of beneficial microbes to face the COVID-19 pandemic Food Res Int 2020; 136: 109577. Jul. 17, 2020.

Alkhater SA. Dynamic Interplay Between Microbiota and Mucosal Immunity in Early Shaping of Asthma and its Implication for the COVID-19 Pandemic. J Asthma Allergy 2020; 13: 369-83. Sep. 2020.

Penninger JM, Grant MB, Sung JJY. The Role of Angiotensin Converting Enzyme 2 in Modulating Gut Microbiota, Intestinal Inflammation, and Coronavirus Infection. Gastroenterology 2021; 160(1): 39-46. Oct. 2020.

Assante G, Williams R, Youngson NA. Is the increased risk for MAFLD patients to develop severe COVID-19 linked to perturbation of the gut-liver axis? J Hepatol 2020. Jun. 2020.

Wang F, Zheng S, Zheng C, Sun X. Attaching clinical significance to COVID-19-associated diarrhea. Life Sci 2020; 260: 118312. Aug. 2020.

Meini S, Zini C, Passaleva MT, et al. Pneumatosis intestinalis in COVID-19. BMJ Open Gastroenterol 2020; 7(1). Jun. 2020.

Carding S, Verbeke K, Vipond DT, Corfe BM, Owen LJ. Dysbiosis of the gut microbiota in disease. Microb Ecol Health Dis 2015; 26: 26191. Feb. 2015.

Alam MT, Amos GCA, Murphy ARJ, Murch S, Wellington EMH, Arasaradnam RP. Microbial imbalance in inflammatory bowel disease patients at different taxonomic levels. Gut Pathog 2020; 12:1. Jan. 2020.

Hegde S, Lin YM, Golovko G, et al. Microbiota dysbiosis and its pathophysiological significance in bowel obstruction. Sci Rep 2018; 8(1): 13044. Sep. 2018.

Canoui E, Ingen-Housz-Oro S, Ortonne N, et al. [Hemophagocytic lymphohistiocytosis with granulomatosis and diffuse T-cell infiltra-

(56) References Cited

OTHER PUBLICATIONS tion associated with disseminated Nocardiosis and pulmonary infection due to *Streptomyces* spp]. Rev Med Interne 2019; 40(7): 457-61. May 2019.

Bolourian A, Mojtahedi Z. *Streptomyces*, shared microbiome member of soil and gut, as 'old friends' against colon cancer. FEMS Microbiol Ecol 2018; 94(8). Jun. 2018.

Gureev AP, Shaforostova EA, Vitkalova IY, et al. Long-term mildronate treatment increased Proteobacteria level in gut microbiome, and caused behavioral deviations and transcriptome change in liver, heart and brain of healthy mice. Toxicol Appl Pharmacol 2020; 398: 115031. Jul. 2020.

Degruttola AK, Low D, Mizoguchi A, Mizoguchi E. Current Understanding of Dysbiosis in Disease in Human and Animal Models. Inflamm Bowel Dis 2016; 22(5): 1137-50. May 2016.

Bamola VD, Ghosh A, Kapardar RK, et al. Gut microbial diversity in health and disease: experience of healthy Indian subjects, and colon carcinoma and inflammatory bowel disease patients. Microb Ecol Health Dis 2017; 28(1): 1322447. Apr. 2017.

Nayfach S, Shi ZJ, Seshadri R, Pollard KS, Kyrpides NC. New insights from uncultivated genomes of the global uuman gut microbiome. Nature 2019; 568(7753): 505-10. Apr. 2019.

Rizzatti G, Lopetuso LR, Gibiino G, Binda C, Gasbarrini A. Proteobacteria: A Common Factor in Human Diseases. Biomed Res Int 2017; 2017: 9351507. Nov. 2017.

Rinninella E, Raoul P, Cintoni M, et al. What is the Healthy Gut Microbiota Composition? A Changing Ecosystem across Age, Environment, Diet, and Diseases Microorganisms 2019; 7(1). Jan. 2019.

Shin NR, Whon TW, Bae JW. Proteobacteria: microbial signature of dysbiosis in gut microbiota. Trends Biotechnol 2015; 33(9): 496-503. Jul. 2015.

Pachikian BD, Neyrinck AM, Deldicque L, et al. Changes in intestinal bifidobacteria levels are associated with the inflammatory response in magnesium-deficient mice. J Nutr 2010; 140(3): 509-14. Jan. 2010.

Suzuki A, Ito M, Hamaguchi T, et al. Quantification of hydrogen production by intestinal bacteria that are specifically dysregulated in Parkinson's disease. PLoS One 2018; 13(12): e0208313. Dec. 2018.

Cattaneo A, Cattane N, Galluzzi S, et al. Association of brain amyloidosis with proinflammatory gut bacterial taxa and peripheral inflammation markers in cognitively impaired elderly. Neurobiol Aging 2017; 49: 60-8. Aug. 2016.

Zaneveld JR, McMinds R, Vega Thurber R. Stress and stability: applying the Anna Karenina principle to animal microbiomes. Nat Microbiol 2017; 2: 17121. Aug. 2017.

Mortensen EM, Coley CM, Singer DE, et al. Causes of death for patients with community-acquired pneumonia results from the Pneumonia Patient Outcomes Research Team cohort study. Arch Intern Med 2002; 162(9): 1059-64. May 2002.

Alanio A, Delliere S, Fodil S, Bretagne S, Megarbane B. Prevalence of putative invasive pulmonary aspergillosis in critically ill patients with COVID-19. Lancet Respir Med 2020; 8(6): e48-e9. May 2020.

Steenwyk JL, Mead ME, de Castro PA, et al. Genomic and phenotypic analysis of COVID-19-associated pulmonary aspergillosis isolates of Aspergillus fumigatus. bioRxiv 2020. Nov. 2020.

Bruno G, Fabrizio C, Buccoliero GB. COVID-19-associated pulmonary aspergillosis: adding insult to injury. Lancet Microbe 2020; 1(3): e106. Jul. 2020.

Lescure FZX, Bouadma L, Nguyen D, et al. Clinical and virological data of the first cases of COVID-19 in Europe: a case series. Lancet Infect Dis 2020; 20(6): 697-706. Mar. 2020.

PCT/US2021/023486, International Search Report and Written Opinion dated Jun. 8, 2021. 12 pages.

Youtube, Italian Covid-19 Patient In Rajasthan Tests Negative After Being Treated With HIV, Swine Flu and Malaria Drugs By Swarajya Staff. Mar. 13, 2020 at 7:10 PM. https://youtu.be/IR_W4s6LoYg News Brief.

Grimwood et al. "Vaccination against respiratory pseudomonas aeruginosa infection". Hum Vaccin Immunother. 2015;11(1):14-20. doi: 10.4161/hv.34296. Nov. 2014.

"French researcher posts successful Covid-19 drug trial." The Connexion. Mar. 17, 2020. https://www.connexionfrance.com/French-news/French-researcher-in-Marseille-posts-successful-Covid-19-coronavirus-drug-trial-results.

Cao et al. "A Trial of Lopinavir-Ritonavir in Adults Hospitalized with Severe Covid-19." The New England Journal of Medicine. The New England Journal of Medicine, vol. 382, No. 19. May 2020. https://www.nejm.org/doi/full/10.1056/NEJMoa2001282?query=featured_home.

Banjanac et al. "Anti-Inflammatory Mechanism of Action of Azithromycin in LPS-Stimulated J774A.1 Cells." Pharmacological Research, vol. 66, No. 4, 2012, pp. 357-362., doi:10.1016/j.phrs.2012.06.011. Jul. 2012.

Cortegiani et al. "A Systematic Review on the Efficacy and Safety of Chloroquine for the Treatment of COVID-19." Journal of Critical Care, doi:10.1016/j.jcrc.2020.03.005. Mar. 2020.

Gao et al. "Breakthrough: Chloroquine Phosphate Has Shown Apparent Efficacy in Treatment of COVID-19 Associated Pneumonia in Clinical Studies." BioScience Trends, vol. 14, No. 1, pp. 72-73., doi:10.5582/bst.2020.01047. Feb. 2020.

Gautret et al. "Hydroxychloroquine and Azithromycin as a Treatment of COVID-19: Results of an Open-Label Non-Randomized Clinical Trial." International Journal of Antimicrobial Agents, p. 105949., doi:10.1016/j.jantimicag .2020.105949. Mar. 2020.

Gupta et al. "Clinical Considerations for Subjects with Diabetes in Times of COVID-19 Epidemic." Diabetes & Metabolic Syndrome: Clinical Research & Reviews, vol. 14, No. 3, pp. 211-212., doi:10.1016/j.dsx.2020.03.002.2020.

Zhang et al. "Potential Interventions for Novel Coronavirus in China: A Systematic Review." Journal of Medical Virology, vol. 92, No. 5, pp. 479-490., doi:10.1002/jmv.25707. Feb. 2020.

Saul, A. "Vitamin C Protects Against Coronavirus", Orthomolecular Medicine News Service, Jan. 26, 2020.

Lightenstein, K. "Can Vitamin C Prevent and Treat Coronavirus?", medicinenet.com. Mar. 9, 2020.

European Patent Application No. 20849772.7. Extended European Search Report dated Oct. 5, 2022. 13 pages.

Sourav Sen Gupta et al.: "Metagenome of the gut of a malnourished child", Gut Pathogens, Biomed Central Ltd, London, UK, vol. 3, No. 1, 20, May 20, 2011.

Knoll et al. "Gut microbiota differs between children with Inflammatory Bowel Disease and healthy siblings in taxonomic and functional composition: a metagenomic analysis", American Journal of Physiology—Gastrointestinal and Liver Physiology, vol. 312, No. 4. Apr. 1, 2017.

Li et al. "Correlation of Gut Microbiome Between ASD Children and Mothers and Potential Biomarkers for Risk Assessment", Genomics Proteomics Bioinfomnatics, vol. 17, No. 1, Apr. 23, 2019.

Duytschaever et al. "Cross-Sectional and Longitudinal Comparisons of the Predominant Fecal Microbiota Compositions of a Group of Pediatric Patients with Cystic Fibrosis and Their Healthy Siblings", Applied and Environmental Microbiology, vol. 77, No. 22. Nov. 2011.

Shapiro et al. "Psoriatic Patients Have a Distinct Structural and Functional Fecal Microbiota Compared with Controls". The Journal of Dermatology. 2019; 46: 595-603 (Year: 2019).

Trujilo. "Actinobacteria". In: eLS. John Wiley & Sons, Ltd: Chichester. DOI: 10.1002/9780470015902.a0020366. pub2, 16 pages (Year: 2016).

Yachida et al. "Metagenomic and Metabolomic Anaylses Reveal Distinct Stage- Specific Phenotypes of the Gut Microbiota in Colorectal Cancer." (Nature Medicine | vol. 25 | Jun. 2019 | 968-976 including methods and extended data, PDF 27 pages total) (Year: 2019).

Qiagen. QlAamp PowerFecal Pro DNA Kit Handbook, Aug. 2017, 24 pages (Year: 2017).

Clemente et al. "The Impact of the Gut Microbiota on Human Health: An Integrative View." (Cell. Mar. 16, 2012; 148(6) 1258-1270) (Year: 2012).

Parracho et al. "Differences Between the Gut Microflora of Children with Autistic Sprectrum Disorders and that of Healthy Childen." Journal of Medical Microbiology (2005), 54, 987-991) (Year: 2005).

(56) References Cited

OTHER PUBLICATIONS

Michiels et al. "Draft Genome Sequence of Acinetobacter Baumannii Strain NCTC 13423, A Multidrug-Resistant Clinical Isolate." Standards in Genomic Sciences. 5 pages. (2016).

Doumatey et al. "Gut Microbiome Profiles are Associated with Type 2 Diabetes in Urban Africans." 13 pages. (2020).

Cole et al. Persistent and Recurrent Clostridium difficile Colitis. Clinics in Colon and Rectal Surgery. vol. 28, No. 2, pp. 65-69. Jun. 2015.

Hedge et al. New advances in the treatment of Clostridium difficile infection (CDI). Therapeutics and Clinical Risk Management. vol. 4, No. 5, pp. 949-964. Oct. 2008.

Loeck et al. Specimen Collection Kits for Norovirus. Nebraska Public Health Laboratory at the University of Nebraska Medical Center. Apr. 2021.

PCT/US2020/044605, International Search Report and Written Opinion dated Feb. 11, 2021. 64 pages.

CUNHA. "Enhanced Efficacy of High Dose Oral Vancomycin Therapy in Closridium Difficile Diarrhea for Hospitalized Adults Not Responsive to Conventional Oral Vancomycin Therapy Antibiotic Stewardship Implications". Journal of Clinical Medicine. Apr. 2018.

Murphy, "Extended Duration Vancomycin in Recurrent Clostridium Difficile Infection: A Systematic Review." 2018.

HOTA. "Oral Vancomycin Followed by Fecal Transplantation Versus Tapering Oral Vancomycin Treatment for Recurrent Clostridium Difficile Infection: An Open-Label, Randomized Controlled Trial." Clinical Infectious Diseases. Nov. 2016.

PCT/US2020/59635. "International Search Report and Written Opinion" dated Mar. 1, 2021.

PCT/US2021/17671. "International Search Report and Written Opinion" dated Apr. 22, 2021.

PCT/US2020/59635. "International Preliminary Report on Patentability" dated Feb. 16, 2022.

Hogue et al. "A Customized At-Home Stool Collection Protocol for Use in Microbiome Studies Conducted in Cancer Patient Populations", Microbial Ecology, vol. 78, Mar. 30, 2019.

Yeoh et al. "Gut microbiota composition reflects disease severity and dysfunctional immune responses in patients with COVID-19." Gut 2021. Jan. 2021.

* cited by examiner

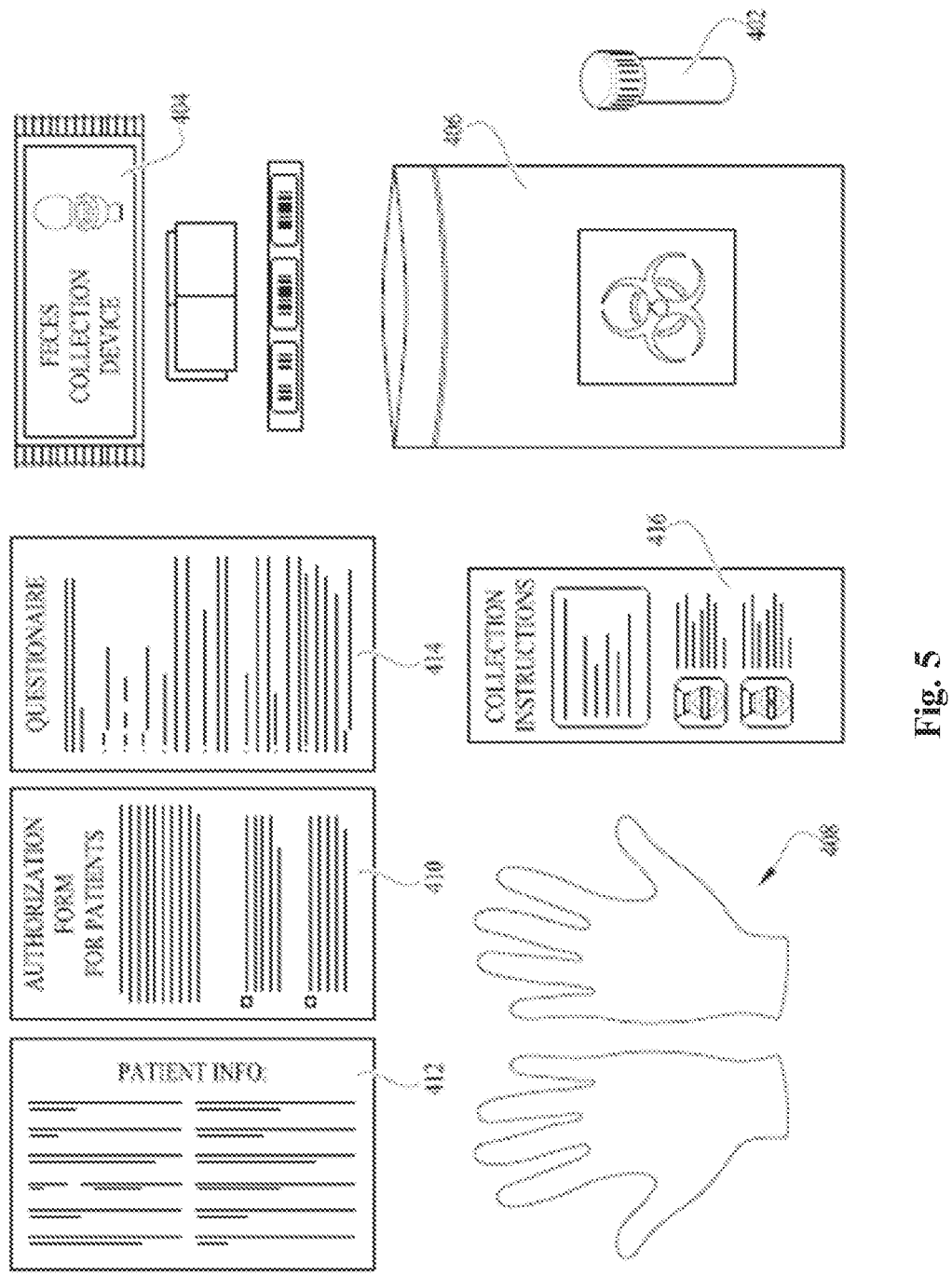

METHODS OF PREVENTING AND TREATING COVID-19 INFECTION WITH PROBIOTICS

CROSS-REFERENCE TO RELATED APPLICATIONS

This application is a continuation-in-part of U.S. Non-Provisional patent application Ser. No. 17/026,051, titled "Method for Preventing and Treating COVID-19 Infection." filed Sep. 18, 2020. This application claims priority to U.S. Provisional Patent Application No. 63/002,486, titled "Method of Analyzing the Microbiome of Individual Stool Samples," filed Mar. 31, 2020, U.S. Provisional Patent Application Ser. No. 62/991,699, titled "Autologous Gastrointestinal Microbiota Preservation," filed Mar. 19, 2020. U.S. Provisional Application Ser. No. 62/991,146, titled "Autologous and Familial Fecal Microbiota Transplant," filed Mar. 18, 2020, and U.S. Provisional Patent Application No. 62/991,190, titled "Method of Analyzing the Microbiome of Individual Stool Samples," filed Mar. 18, 2020. The contents of all of these applications are incorporated by reference in their entirety.

BACKGROUND

The human gastrointestinal (GI) microbiome is a complex, interconnected web of microbes, living in a symbiotic relationship with their host. There are greater than ten times more bacteria in the human body than there are human cells, all in a delicate and ever-changing balance to maintain a healthy GI tract. When this balance is disrupted, a condition known as dysbiosis, or disease, can occur. Traditional methods of treating disease and infection include the use of prescription medications, which come with potentially serious side effects and other issues.

COVID-19 is a novel betacoronavirus that originated in bats in the city of Wuhan, China. This disease has rapidly spread to become a worldwide pandemic, as declared by the World Health Organization (WHO). Symptoms of COVID-19, including fever, myalgia, coughing and shortness of breath, may appear from 2 and 14 days after exposure. Approximately 20% of patients progress to severe illness, including pneumonia, respiratory distress, and even death. Cases in the US have increased five-fold over the last week, alone. The disease is spreading rapidly, and a cure is desperately needed.

Thus, there is a significant unmet need for preventing and treating COVID-19 infection.

SUMMARY

The present invention addresses this need. In a first embodiment, the present invention is directed to my method of preventing COVID-19 infection in an individual. The method comprises screening the individual to determine whether the individual is infected with COVID-19; and administering at least one probiotic.

The probiotic comprises one or more of the following microorganisms: *Bifidobacterium, Clostridium, Veillonella, Ruminococcus*, and *Sutterella*.

Optionally, the probiotic further comprises a bacterium selected from the actinobacteria phylum.

The probiotic can be administered in or more of the following forms: fecal transplant, suppository, or orally.

The method of administering the probiotic via fecal transplant can comprise the following additional steps: b) acquiring a fecal sample from the individual; c) processing the fecal sample from the individual; d) sequencing the fecal sample from the individual to determine the individuals microbiome: e) analyzing the sequenced fecal sample; f) administering one or more of the following to the individual: at least one antibiotic and at least one antiparastic; f) performing the fecal microbiota transplant, and g) monitoring the individual.

The antibiotic is vancomycin, doxycycline, or xiafan, and the antiparasitic is ivermectin.

The step of acquiring the fecal sample comprises use of a stool sample collection kit or colonoscopy. The stool sample kit comprises: a) at least one stool sample collection vial, b) at least one toilet accessory or seat cover; c) at least one specimen bag; d) at least one pair of gloves; e) an authorization form; f) a patient information card; g) a questionnaire; and h) stool sample collection instructions.

The step of administering vancomycin can comprise administering 250 mg of liquid vancomycin to the individual every 8 hours for 10 consecutive days.

Optionally, the step of administering the vancomycin comprises administering 250 mg of liquid vancomycin to the individual every 8 hours for 6 consecutive weeks.

The suppository is in the form of a liquid dosage, a solid dosage, or a semi-solid dosage.

The oral probiotic is in the form of a pill/lozenge, liquid tincture or drink, chewable In a second embodiment, the present invention is directed to a probiotic for preventing and treating COVID-19 infection in an individual. The probiotic comprises at least one of the following microorganisms: *Bifidobacterium, Clostridium. Veillonella, Ruminococcus*, and *Sutterella*.

Optionally, the probiotic comprises at least one of each of the following microorganisms. *Bifidobacterium, Clostridium, Veillonella. Ruminococcus*, and *Sutterella*.

The probiotic can be administered via fecal transplant, suppository, or orally.

DRAWINGS

These and other features, aspects and advantages of the present invention will be better understood with reference to the following description, appended claims, and accompanying drawings where:

FIG. 5 is top plan view of the stool collection kit of FIG. 4, wherein the contents have been removed from the box.

DETAILED DESCRIPTION

Figure 1:
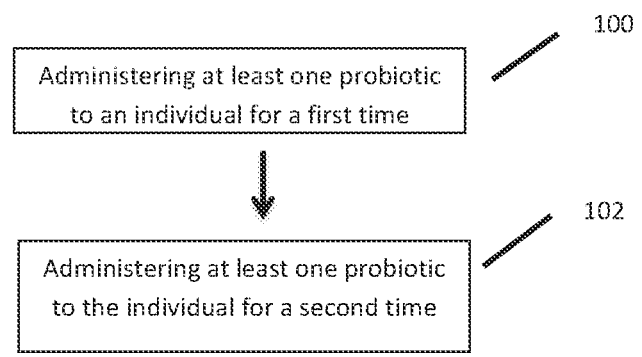
FIG. 1 is a flow chart of a method of preventing COVID-9 infection in an individual by administering probiotics.

The following discussion describes in detail one embodiment of the invention and several variations of that embodiment. This discussion should not be construed, however, as limiting the invention to those particular embodiments. Practitioners skilled in the art will recognize numerous other embodiments as well.

Definitions

As used herein, the following terms and variations thereof have the meanings given below, unless a different meaning is clearly intended by the context in which such term is used.

The terms "a," "an," and "the" and similar referents used herein are to be construed to cover both the singular and the plural unless their usage in context indicates otherwise.

As used in this disclosure, the term "comprise" and variations of the term, such as "comprising" and "comprises," are not intended to exclude other additives, components, integers, ingredients or steps.

The term "probiotic" as used herein means a probiotic substance or preparation; a microorganism (or combination of microorganisms) introduced into the body for its beneficial qualities.

The term "microorganism" as used herein means a microscopic organism, including a bacterium, virus, or fungus.

Referring now to the drawings, wherein like reference numerals designate identical or corresponding features throughout the several views. Further, described herein are certain non-limiting embodiments of my pipeline filter assembly for pool filtering and maintenance.

The following discussion describes in detail multiple embodiments of the invention with several variations of those embodiments. This discussion should not be construed, however, as limiting the invention to those particular embodiments. Practitioners skilled in the art will recognize numerous other embodiments as well.

Referring now to FIG. 1, there is shown a first embodiment of the present invention, which is directed to a method of preventing COVID-19 infection in an individual by administering probiotics. The method of prevention comprises the step of administering 100 at least one probiotic to an individual. Optionally, the probiotic can be administered more than one time 102.

Figure 2:
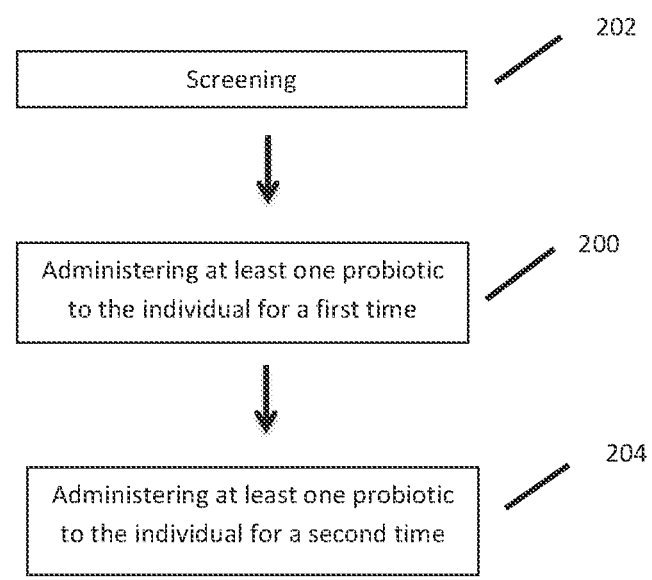
FIG. 2 is a flow chart of a method of treating an individual infected with COVID-19 by administering probiotics.
Figure 3:
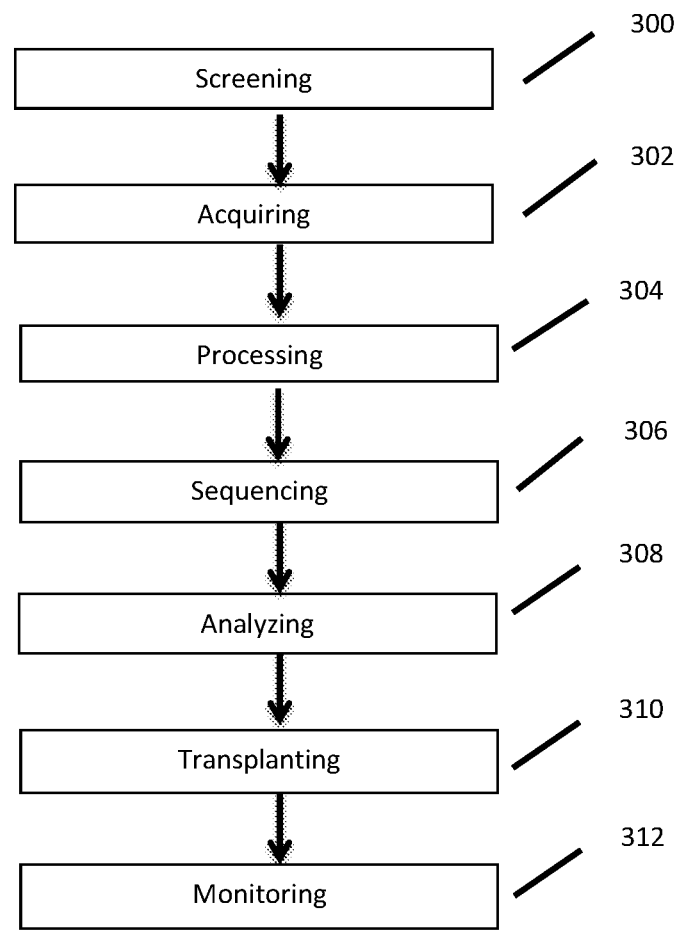
FIG. 3 is a flow chart of a method of treating an individual infected with COVID-19 with fecal microbiota transplant, having features of the present invention.

Referring now to FIG. 2, there is shown a second embodiment of the present invention, which is directed to a method of treating COVID-19 infection in an individual by administering probiotics. The method of treatment comprises administering 200 at least one probiotic to an individual infected with COVID-19. Optionally, the individual is first screened 202 for infection with COVID-19 prior to administration of the probiotics. Optionally, the probiotic can be administered more than one time 204.

In both embodiments, the probiotics can comprise any of the bacteria listed in Example 6. More specifically, the probiotics can comprise one or more of the following. *Bifidobacterium, Clostridium, Veillonella, Ruminococcus, Sutterella, Faecalibacterium,* and *Erysiplatoclostridium* at the species and genus levels, Bifidobacteriaceae, Veilloneacellae, Sutterellaceae, Prevotellaceae and Erysipelotrichaceae at the family level, Bifidobacteriales, Veillonellales, Burkholderiales, and Erysipelotrichales at the order level, Actinobacteria, Negativicutes, Betaproteobacteria, and Erysipelotrichia class level and more importantly, Proteobacteria and Actinobacteria at the phylum level.

The probiotics can be administered via the following methods: fecal transplant, suppository, or orally in the form of a pill/lozenge, liquid tincture or drink, chewable tablet, food stuff such as yogurt, or pressurized spray. The suppository can be in form of a liquid dosage (e.g., enemas), solid dosage (e.g., suppositories, capsules, and tablets), and semi-solid dosage (e.g., gels, foams, and creams). The various methods listed above of administering the probiotics are not exclusive of each other. As such, any combination of the above methods of administering the probiotic can be used.

The above listed bacteria can be given to the patient singly (e.g. the probiotic only contains one type of bacteria), or the probiotic can contain one or more of the bacteria listed above plus multiple other microbes like fecal material (meaning as a fecal transplant).

The methods of the present invention can be used to prevent and treat a plurality of diseases, including but not limited to COVID-19/corona virus infection, skin cancer, *Clostridioides difficile* Infection. Obesity. Alzheimer's Disease, Crohn's Disease. Myalgic Encephalomyelitis/Chronic Fatigue Syndrome (ME/CFS), Psoriasis, Chronic Urinary Tract Infections, Ulcerative Colitis, Multiple Sclerosis, Chronic Constipation, Lyme Disease, Celiac Disease. Parkinson's Disease, Elevated Cholesterol, Colorectal Cancer. Amyotrophic Lateral Sclerosis (ALS), Fatty Liver, Rheumatoid Arthritis, Anxiety, Obsessive-Compulsive Disorder, Bipolar Disorder, Migraine Headaches, Depression, Diabetes Mellitus, Lupus, Epidermolysis Bullosa. Metastatic Mesothelioma, Eczema, Acne, Irritable Bowel Syndrome, Myasthenia Gravis, Gout, and Autism Spectrum Disorders.

The human gastrointestinal (GI) microbiome is a complex, interconnected web of microbes, living in a symbiotic relationship with their host. There are greater than ten times more bacteria in in the human body than there are human cells in the human body, all in a delicate and ever-changing balance to maintain a healthy GI tract. When this balance is disrupted, a condition known as dysbiosis, or disease, can occur. There is still a debate over whether dysbiosis is a cause of disease or a symptom of it. Naturally, since the microbiome has such a profound impact on human health, including helping humans digest food, make vitamins, and teach human immune cells to recognize pathogens, it plays a vital role in maintaining health. By manipulating the microbiome of patients with disease or infection-induced dysbiosis, the patient's microbiome can be restored to a pre-infection state.

The present invention accomplishes this restoration by administering probiotics via one of the three methods outlined above. One of the methods of administration is fecal microbiota transplant. The transplants can autologous, meaning utilizing the patient's own stool, collected and stored prior to infection, familial, meaning utilizing a family members stool, or third party donor, meaning the stool is collected from a screened, matched donor that is unrelated to the patient.

In general, the method of administering the probiotics via fecal transplants comprises the following steps: screening the individual/patient 300, acquiring a fecal sample from the individual/patient 302, processing the fecal sample from the patient 304, sequencing the fecal sample from the patient 306, analyzing the sequenced fecal sample 308, performing the fecal microbiota transplant 310, and monitoring the patient 312. However, not all of the steps may be required, and the steps of the method of the present invention can vary depending on whether the transplant is autologous, familial, or third party.

Autologous Fecal Transplant

The autologous fecal transplant method comprises three main: screening the patient 300, acquiring a sample from the patient 302, and transplanting the patient's own fecal microbiota into the patient 310.

During the step of screening 300, the patient undergoes the following: signing of the consent form, providing their medical history and demographics, having an EKG performed, having their vital signs taken/read, providing their height and weight, and providing the staff with a list of their prior and concomitant medications. Concomitant medications include any form of antibiotics, probiotics, or opiates.

The doctor or staff overseeing the procedure verifies all inclusion and no exclusion criteria are met.

The patient may continue to take medications currently prescribed; however, the patient must be able to discontinue antibiotics prior to fecal microbiota transplant.

The patient must agree to discontinue use of outside probiotics; however, consumption of active culture yogurt is permissible.

The patient must agree to utilize either a barrier contraception method with spermicide or an IUD (intra-uterine device) for the duration of the study.

The exclusion criteria comprise the following:

The patient refuses to sign the informed consent form.

The patient has a history of total colectomy with ileorectal anastomosis or proctocolectomy.

The patient has a postoperative stoma, ostomy, or ileoanal pouch.

The patient has short bowel syndrome.

The patient is scheduled for a bowel resection.

The patient has had a bowel perforation within six months of screening.

The patient has known symptomatic obstructive strictures.

The patient was exposed to oral or parenteral antibiotics in the four weeks prior to screening, with the exception of topical antibiotics, which are permitted.

The patient has a positive serology for Hepatitis B, Hepatitis C, or HIV.

The patient is currently diagnosed with, or has a history of, uveitis diagnosed by an optometrist or an ophthalmologist.

The patient has a history of malignancy in the last five years, excluding basal cell carcinoma of the skin or carcinoma in situ of the cervix that has been treated with no evidence of recurrence.

The patient has undergone treatment with total parenteral nutrition.

The patient has a history of active tuberculosis requiring treatment in the past three years.

The patient has a history of drug or alcohol abuse within the past three years.

The patient is a female who is pregnant, intends to become pregnant, or is lactating. This is due to unknown fetal or child effects.

The patient has an inability to adequately communicate with the investigator or their respective designee and/or comply with the requirements of the entire study.

The patient participated in any experimental drug protocol within the past twelve weeks.

The patient has clinically significant abnormalities in hematology or biochemistry as confirmed by repeat testing based on investigator's discretion.

Bloodwork is also performed on the patient, which includes the following: a blood mycobacterial culture, which is a test to look for the bacteria that cause tuberculosis and other infections caused by similar bacteria, a complete blood count, a chemistry panel, and a C-reactive protein test. C-reactive protein (CPR) is a blood test marker for inflammation in the body. CRP is produced in the liver and its level is measured by testing the blood. CRP is classified as an acute phase reactant, which means that its levels will rise in response to inflammation.

The patient undergoes a urinalysis, a fecal calprotectin test, and uveitis screening.

Fecal calprotectin is a biochemical measurement of the protein calprotectin in the stool. Elevated fecal calprotectin indicates the migration of neutrophils to the intestinal mucosa, which occurs during intestinal inflammation, including inflammation caused by inflammatory bowel disease.

Uveitis is a form of eye inflammation. It affects the middle layer of tissue in the eye wall (uvea). Uveitis warning signs often come on suddenly and get worse quickly. Warning signs include eye redness, pain and blurred vision. The condition can affect one or both eyes.

Once all the above has been performed by the doctor/ provided by the patient, the doctor provides the patient with at least one stool collection kits and instructs the patient on use of the stool collection kits.

Figure 4:
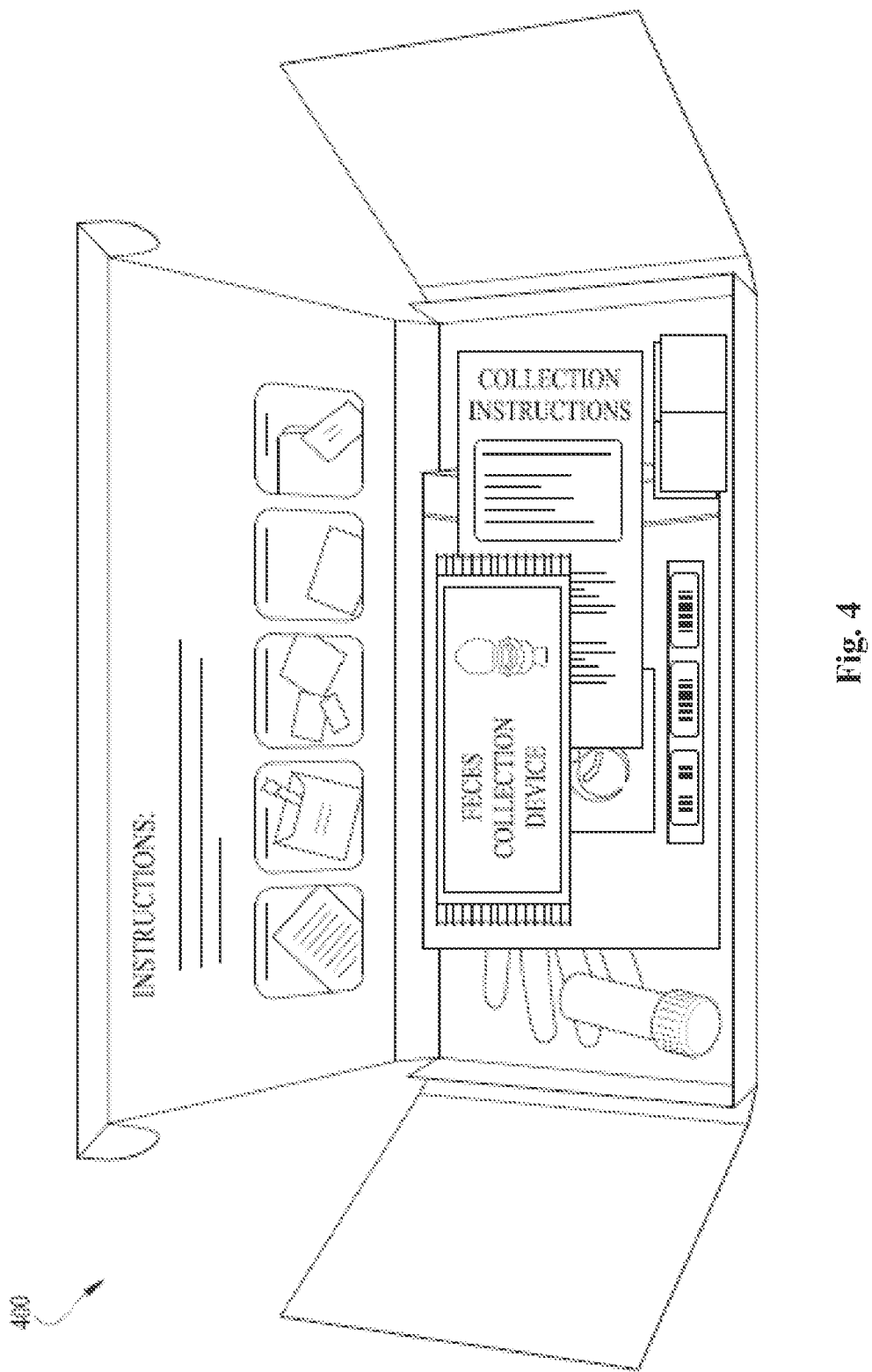
FIG. 4 is a top plan view of a stool collection kit having features of the present invention.

During the step of acquiring a sample 302, regardless of the disease from which the patient is suffering, the following takes place: The step of acquiring a stool sample 302 can either involve the stool sample collection kit 400 or a colonoscopy. The stool sample collection kit 400 is shown in FIGS. 4 and 5 and comprises: at least one stool sample collection vial 402, optionally the vial 402 contains a spoon, at least one toilet accessory or seat cover 404, at least one specimen bag 406, at least one pair of gloves 408, an authorization form 410, a patient information card 412, a questionnaire 414, and stool sample collection instructions 416.

The toilet accessory 404 is in the form of a circular strip of paper that slips over the toilet seat and creates a raised platform on which to provide the voided stool sample.

The stool sample collection instructions 416 are as follows: (1) Correctly position the toilet accessory (i.e. toilet cover) over the toilet seat and put on disposable latex gloves. (2) Unscrew the collection tube cap and use the spoon to scoop one spoonful of the stool sample from the feces. Do not pass the stool sample into the toilet or directly into the collection vial, and do not mix urine or water with the stool sample. (3) Place the stool sample into the collection vial. (4) Tighten the cap and shake to mix the contents thoroughly (and/or invert 10 times) to create a suspension. Some fecal material may be difficult to re-suspend. As long as the stool sample is suspended, the sample is stabilized. Foaming/ frothing during shaking is normal. (5) Place the collection vial in the bag labeled "Specimen Bag-Biohazard" and seal the bag. (6) Place the bag back in the collection kit box. (7) Remove toilet cover and let it fall into the toilet bowl. Flush both the toilet cover and excess stool down the toilet. (8) Remove and dispose of gloves. Thoroughly wash hands.

The sample is then processed 304, the microbiome of the sample is sequenced 306 and analyzed 308, and the sample is stored for future use.

In summary, the stool is processed 304 via the following steps:

First, a stool is collected from the patient via an anaerobic method as noted above so that the stool is not exposed to air.

Second, the stool is processed anaerobically in a blender in an anaerobic chamber with normal saline.

Third, the container that the stool is in is kept sealed and stored in a freezer at minus 80 degrees F. until needed for a transplant.

Preferably, the stool sample is stored in a facility much like a sperm bank where individuals can donate their individual stool samples for storage. Most preferably, although not always possible, the individual donates a stool sample (healthy baseline microbiome sample) at birth or at an early stage in life. Optionally, the baseline sample is provided later in life, but pre-hospitalization or pre-epidemic, when the individual is in a healthy state. The purpose is to bank a sample of the individual's healthy microbiome in the event the individual becomes unhealthy and requires a fecal transplant utilizing the healthy sample to reestablish a healthy microbiome. Re-establishing a healthy microbiome will assist the individual in overcoming the current disease, infection, or epidemic.

A more detailed discussion of the processing 304 and sequencing 306 steps are as follows. For these two steps, the following equipment is utilized: centrifuges, pipettes, thermocycler, fluorometers, vortexers, refrigerators/freezers, and a sequencing system (for example, an Illumina NextSeq 550 Sequencing System).

The step of processing the sample 104 includes extracting and purifying patient DNA from the sample. Individual patient DNA is extracted and purified with a DNA extraction kit. Optionally, the QIAmp® PowerFecal® Pro DNA Kit can be used. The DNA extraction kit isolates both microbial and host genomic DNA from stool and gut samples.

In summary, for the DNA extraction step, the stool samples are added to a bead beating tube for rapid and thorough homogenization. Cell lysis occurs by mechanical and chemical methods. Total genomic DNA is captured on a silica membrane in a spin-column format. DNA is then washed and eluted from the membrane and ready for NGS, PCR and other downstream application.

Once the DNA has been extracted, the DNA is then quantitated using a fluorometer. The fluorometer can be a dual-channel fluorometer for nucleic acid quantitation. It provides highly sensitive fluorescent detection when quantifying nucleic acids and proteins.

The following steps are performed when quantitating the sample:

Mix 1-20 microliters of the extracted DNA sample and 200 microliters of dye in a 0.5 ml PCR tube. Mix well by pipetting or vortexing.

The fluorescence is then measured and the nucleic acid concentration is calculated and/or displayed.

Next, the library is prepared. The assay of the present invention is designed to detect all bacteria, viruses, and fungi that reside in the microbiome of the stool samples being evaluated. The assay utilizes an enzymatic reaction to fragment the DNA and to add adapter sequences. Library fabrication includes tagmentation, tagmentation clean-up, and an amplification step followed by another clean-up prior to pooling and sequencing.

The following definitions and abbreviations are used in this section:
BLT: Bead-Linked Transposomes
DNA: Deoxyribonucleic Acid
EPM: Enhanced PCR Mix
EtOH: Ethanol
NGS: Next Generation Sequencing
NTC: No Template Control
PCR: Polymerase Chain Reaction
RSB: Resuspension Buffer
SPB: Sample Purification Beads
TB1: Tagmentation Buffer
TSB: Tagment Stop Buffer
TWB: Tagment Wash Buffer First, the BLT and TB1 are brought up to room temperature. Then, the BLT and TB1 are vortexed to mix.

Next, the appropriate volume of DNA is added to each well so that the total input amount is 100 nanograms. The optimal input for this assay is 100 nanograms, however, less DNA input can be utilized.

Next, the appropriate volume of nuclease-free water is added to the DNA samples to bring the total volume to 30 microliters.

Then, the BLT is vortexed vigorously for 10 seconds. Next, 11 microliters of BLT and 11 microliters of TB1 are combined for each sample, creating a tagmentation mastermix. Overage is included in this volume.

Next, the tagmentation master mix is vortexed and the volume is equally divided into an 8-tube strip.

Next, 20 microliters of the tagmentation master mix is transferred to each well containing a sample.

Then, the plate is sealed with Microseal 'B' and placed on a thermo cycler preprogrammed with the TAG program. The thermo cycler has a heated lid at 100° C. and reaction volume set to 50 microliters.

Next, the TAG program is run as shown in Table 1:

TABLE 1

| Cycle Step | Temperature | Time |
| --- | --- | --- |
| Step 1 | 55° C. | 15 minutes |
| Step 2 | 10° C. | ∞ |

Once the TAG program is complete, the plate is removed from the thermo cycler.

Next, the Microseal 'B' seal is removed and 10 microliters of TSB is added to each sample.

Next, the plate is sealed with a Microseal 'B' and placed on the thermo cycler preprogrammed with the PTC program. The thermo cycler has a heated lid at 100° C.

Next, the PTC program is shown in Table 2:

TABLE 2

| Cycle Step | Temperature | Time |
| --- | --- | --- |
| Step 1 | 37° C. | 15 minutes |
| Step 2 | 10° C. | ∞ |

When the PTC program is complete, the plate is removed from the thermo cycler and placed on a magnetic stand. The plate is left on the magnetic stand for about 3 minutes (as long as it takes for the solution to clear).

Once the solution is clear, the Microseal 'B' is removed from the plate and the supernatant is removed and discarded.

Next, the plate is removed from the magnetic stand and about 100 microliters of TWB is added. The sample should be pipetted slowly until the beads are fully re-suspended.

Next, the plate is placed back on the magnetic stand and approximately 3 more minutes pass while the solution clears again.

Once the solution clears, the supernatant is removed and discarded.

Next, the plate is removed from the magnetic stand and about 100 microliters of TWB is added. The sample should be pipetted slowly until the beads are fully re-suspended.

Next, the plate is again placed on the magnetic stand for an additional 3 minutes while the solution clears.

Next, 22 microliters of EPM and 22 microliters of nuclease-free water are combined with each sample to form a PCR mastermix. Overage is included in this volume. The PCR mastermix is vortexed and centrifuged.

With the plate on the magnetic stand, the supernatant is removed and discarded.

Next, the plate is removed from the magnetic stand and 40 microliters of PCR mastermix are immediately added directly onto the beads in each sample well.

The mastermix is immediately pipetted until the beads are fully re-suspended. Alternatively, the plate is sealed and a plate shaker is used at 1600 rpm for 1 minute.

Next, the plate is sealed with a Microseal 'B' and centrifuged at 280×g for 3 seconds.

Next, 10 microliters of index adapters are added to each sample in the plate. The plate is then centrifuged at 280×g for 30 seconds.

Next, the plate is placed on the thermo cycler that is preprogrammed with the BLT PCR program (and with lid preheated at 100° C.).

The BLT PCR Program is run as shown in Table 3:

TABLE 3

| Cycle Step | Number of Cycles | Temperature | Time |
| --- | --- | --- | --- |
| Step 1 | 1 | 68° C. | 3 minutes |
| Step 2 | 1 | 98° C. | 3 minutes |
|  |  | 98° C. | 45 seconds |
| Step 3 | 5 | 62° C. | 30 seconds |
|  |  | 68° C. | 2 minutes |
| Step 4 | 1 | 68° C. | 1 minute |
| Step 5 | 1 | 10° C. | ∞ |

When BLT PCR program is complete, the plate is removed from the thermo cycler and centrifuged at 280×g for 1 minute.

Next, the plate is placed on the magnetic stand and it takes about 5 minutes for the solution to clear.

Next, about 45 microliters of supernatant are transferred from each well of the PCR plate to the corresponding well of a new midi plate.

Then, the midi plate is vortexed and the SPB is inverted multiple times to re-suspend.

Next, about 40 microliters of nuclease-free water is added to each sample well containing supernatant.

Next, about 45 microliters of SPB is added to each sample well. Each sample well is then mixed.

The plate is then sealed and incubated for 5 minutes at room temperature.

Next, the plate is placed on the magnetic stand and it takes about 5 minutes for the solution to clear.

Next, the SPB is vortexed thoroughly and 15 microliters of SPB is added to each well of a new midi plate.

Then, 125 microliters of supernatant is transferred from each well of the first plate into the corresponding well of the second midi plate containing 15 microliters SPB.

Each well of the second midi plate is then mixed and the first midi plate can be discarded.

The second midi plate is sealed and incubated for 5 minutes at room temperature.

The second midi plate is placed on the magnetic stand and it takes about 5 minutes for the solution to clear.

Next, without disturbing the beads, the supernatant is removed and discarded.

While the midi plate is still on the magnetic stand, 200 microliters of fresh 80% EtOH are added to the plate, without mixing. The plate is then incubated for 30 seconds.

Next, without disturbing the beads, the supernatant is removed and discarded.

While the second midi plate is still on the magnetic stand, about 200 microliters of fresh 80% EtOH are added, without mixing. The plate is then incubated for 30 seconds.

Next, without disturbing the beads, the supernatant is removed and discarded. Any residual EtOH is also removed and the second midi plate is allowed to air dry on the magnetic stand for about 5 minutes.

The second midi plate is removed from the magnetic stand and about 32 microliters of RSB is added to the beads.

The second midi plate is then re-suspended and incubated for about 2 minutes at room temperature.

The second midi plate is placed back on the magnetic stand it takes about 2 minutes for the solution to clear.

Once the solution clears, about 30 microliters of supernatant are transferred to a new 96-well PCR plate.

Next, the library is pooled and sequenced.

The following definitions and abbreviations are used in this section:

DNA: Deoxyribonucleic Acid
EtOH: Ethanol
HTI: Hybridization Buffer
NGS: Next Generation Sequencing
NTC: No Template Control
RSB: Resuspension Buffer
SAV: Sequencing Analysis Viewer The following steps are taken to sequence the DNA 106:
1. Prepare the reagent cartridge for use.
2. Denature and dilute sample libraries.
3. Load pooled sample DNA libraries into the prepared reagent cartridge.
4. Set up and start the DNA sequencing using the selected DNA sequencing machine. The sequencing run can take approximately 27-30 hours to complete.

The bioinformatics pipeline utilizes a computational tool that profiles the microbial communities from metagenomic sequencing data with species level resolution. Patient microbiome profiles are analyzed to ascertain not only the profile of microbes in patient samples but also to identify specific strains, and provide accurate estimation of organismal abundance relative to the overall diversity Once the DNA is sequenced, the microbiome the individual patient is analyzed 308. The step of analyzing 308 the microbiome of the individual can include the following: comparing the microbiome of the individual to the microbiome of the individual's mother, comparing the microbiome of the individual to the microbiome of a sibling of the individual, comparing the microbiome of the individual with a health condition to the microbiome of another individual with same health condition, and comparing the microbiome of the individual with a health condition to the microbiome of the individual before they acquired the health condition (otherwise referred to as baseline versus non-baseline).

If the individual's baseline microbiome is being used in the analysis step 308, then the above recited steps of acquiring a stool sample 302, processing the stool sample 304, and sequencing the microbiome of the individual 306 are performed at least twice—once before the individual acquires a health condition (known as a baseline) and at least once after the individual acquired the health condition. This is necessary so that the baseline microbiome can be compared to the microbiome when the individual is suffering from a health condition.

Optionally, the steps of acquiring a stool sample 302, processing the stool sample 304, and sequencing the microbiome of the individual 306 are performed for a third time, after the individual has overcome the health condition, to confirm that the individual is healthy again.

During the step of transplanting fecal microbiota 310, the following takes place: When the patient suspects they are out of remission, from whatever disease they are suffering from, they return to the doctor's office for the following; vital signs are taken/read, an EKG is performed, their height and weight is recorded, they provide the doctor with an updated list of prior and concomitant medications, and their bloodwork is also repeated. A urinalysis, a fecal calprotectin test, and a uveitis screening are also performed.

Next, the autologous fecal microbiota transplant is scheduled. The patient is also provided with colonoscopy preparation instructions and a bowel cleanse prescription.

Optionally, prior to performing the transplant 310, the patient receives an antibiotic and/or antiparasitic treatment. The antibiotic can comprise one or more of the following: vancomycin, doxycycline, and xifaxan. The antiparasitic can comprise ivermectin.

The antibiotic/antiparasitic treatment can be for a period of 1 to 10 days or up to 6-weeks, and any length of time in between. The dose of antibiotic/antiparasitic is 250 mg of liquid suspension (formulated in a concentration of 500 mg/6 mL) administered orally every 8 hours.

When the patient returns for the transplant, the patient arrives at the surgical center prepped and fasted. The patient signs the informed consent form, and the fecal microbiota transplant is conducted.

The fecal microbiota transplant 310 comprises the following steps:

First, the stool material from the blender is thawed and the probiotics are added. The resulting mixture is placed in syringes anaerobically.

Second, the patient is brought into a surgical suite and sedated in order to perform a colonoscopy.

Third, the patient is placed in the Trendelenburg position, where the body is laid supine, or flat on their back on a 15-30 degree incline with their feet elevated above their head.

Fourth, the mixture of fecal material and probiotics is injected into the cecum.

Fifth, the patient is given atropine or diphenoxylate and loperamide for one week to slow the colon so that the stool material will remain inside the digestive tract.

And finally, if a colonoscopy cannot be performed then the blended stool material mixed with the probiotics is administered to the patient via a nasogastric tube or placed in capsules that patient swallows and are then dissolved in cecum.

Once the transplant 310 is completed, the patient is then monitored 312. The step of monitoring 312 involves monitoring the patient for a short period of time before being discharged and returning to the doctor for at least two follow-up visits. The first follow-up visit is typically 28 days after the transplant.

During the first follow-up visit, the patient undergoes a physical examination, their height and weight are recorded, their vital signs are taken/read and an EKG is performed. Additionally, the patient provides the staff with an updated list of prior and concomitant medications, a stool sample is collected for microbiome analysis, and fecal calprotectin is tested.

The second follow-up visit is typically 28 days after the first follow-up visit. During the second follow-up visit the patient undergoes a physical examination, their height and weight are recorded, and the doctor reviews both the microbiome results and the fecal calprotectin result with the patient. The patient provides the doctor with an updated list of prior and concomitant medications. If the microbiome results are satisfactory, stool will be collected for future autologous fecal microbiota transplant to be done every 6 months.

Familial Fecal Transplant

In the event the transplant is a familial transplant, the family member is the stool donor, the individual supplying the stool sample administered to the patient during the fecal microbiota transplant. As such, the family member that is the stool donor undergoes the screening steps 300 outlined above to ensure the family member does not suffer from the disease or infection, and the acquiring a sample steps 302 outlined above.

Preferably, the family member also undergoes the processing 304, sequencing 306, and analyzing 308 steps outlined above to ensure the familial member is a good match for the patient.

Once the familial stool sample has been collected, the patient receiving the sample then undergoes the transplant 310 and monitoring steps 312 outlined above.

Third Party Donor Fecal Transplant

In the event the transplant is a third party donor transplant, the third party is stool donor, the individual that is supplying the stool sample administered to the patient during the fecal microbiota transplant. As such, the third party undergoes both the screening 300 and the acquiring 302 steps outlined above.

Preferably, the third party donor also undergoes the processing 304, sequencing 306, and analyzing 308 steps outlined above to ensure the third party donor is a good match for the patient.

Once the third party donor stool sample has been collected, the patient receiving the sample then undergoes the transplant 310 and monitoring 312 steps outlined above.

Optionally, as discussed above, the probiotics can be administered to the individual via in the form of a suppository, or orally in the form of a pill/lozenge, liquid tincture or drink, chewable tablet, food stuff such as yogurt, or pressurized spray.

In all instances, amount of probiotic, and the amount or dosage of the bacteria contained within the probiotic can vary from patient to patient, depending on the microbiome needs. The probiotics can be administered for as many days as the supervising physician deems necessary.

Results from the Various Transplant Studies;

An individual infected with COVID-19 can be treated by administering a probiotic containing at least one of the following (or any combination of the same): *Bifidobacterium, Clostridium, Veillonella, Ruminococcus,* and *Sutterella*.

Optionally, the above listed bacteria can be administered to the individual orally in form of a pill or spray, or rectally, in the form of a fecal transplant, suppository, or cream.

Optionally, the probiotic can further include any bacteria that are part of the actinobacteria phylum.

If the transplant is familial, then the stool sample utilized during the transplant comes from a donor that is not the patient themselves, but rather a genetically related family member. With respect to the third party donor, the third party donor is not genetically related to the patient.

In both instances, either the family member or the third party donor donates and stores the sample per the protocol described above. When the patient requires a FMT, the appropriate donor sample is selected and administered to the patient. This is considered a matched donor as their microbiome sequences have been "matched." To achieve successful GR, a detailed patient analysis is performed, as well as meticulous, precise donor selection. There must be a specific match between patient and donor.

Preferably, the donor/third party is genetically related to the patient.

An individual person's microbiome is an accumulation of bacterial DNA, viral DNA, and fungal DNA. The types, quantity and balance of microbes in a person's microbiome are unique to that individual and can affect their susceptibility or resistance to a variety of health issues. The personal microbiome of an individual is as unique to an individual as a fingerprint.

Finding donors is the most critical, and complex, aspect of treatment, and the most important aspect is to precisely match the donor.

Every human being has a unique microbiome in their gut. This is why finding an appropriate donor is extremely complicated and critical to healing. Donor match is the most important factor because if it is not precise, "the same thing that cures a disease can also cause disease."

EXAMPLES

Example 1: Vancomycin and Familial Fecal Microbiota Transplant for the Treatment of Subjects with Crohn's Disease Objectives: Improve the core features of Crohn's disease, including the short and long-term effects of the outcomes; Assess gastrointestinal microbiome relative abundance before and after familial fecal microbiota transplant using whole genome shotgun sequencing; Assess safety and tolerability of familial fecal microbiota transplant in subjects with Crohn's disease.

Procedure: Patients with Crohn's disease are treated with vancomycin followed by familial fecal microbiota transplant (FFMT). The vancomycin is prescribed at the second baseline visit and is given for 10 days. For FFMT, the donor provides a fresh stool sample the morning of the procedure. The sample is brought by the donor to the study site for processing. Processing includes emulsification with sterile normal saline at a 1:1 ratio to create a fecal slurry.

Following the FFMT by colonoscopy the caregiver is taught how to prepare and administer the FFMT enemas at home (during the week 4 visit). Table 4 documents the treatment protocol.

TABLE 4

| Intervention Name | Vancomycin | Familial Fecal Microbiota Transplant |
|---|---|---|
| Dose Formulation | Suspension of 83 mg/mL (500 mg/6 mL) | Emulsification |
| Route of Administration | Oral | Delivered to the colon directly by colonoscope in the first transplant, and by enema in all subsequent transplants |

Statistical Analysis. The statistical evaluation is performed by an outside statistician using SAS® version 9.3 or higher (Statistical Analysis System, SAS Inc., Cary, N.C.) software package. Descriptive summaries are given by treatment group and/or overall. The number of subjects within each treatment group of the analysis set is given in each table. Categorical variables are summarized with counts (n) and percentages (%), together with the number of non-missing values. Fisher's exact test for categorical variables is used. The number of non-missing values is used as the denominator for the calculation of percentages. Incidence of adverse events is based on the number of subjects in the respective analysis set and treatment group. Descriptive statistics for continuous variables are comprised of the number of non-missing observations (n), mean, standard deviation (SD), median, minimum (Min) and maximum (Max), if not otherwise stated. Student's t-test and Mann-Whitney for continuous parametric and nonparametric variables are used respectively. ANOVA is used for comparing means between individual groups. When applicable, these summaries are provided by visit. In case of premature withdrawal from the trial, efficacy and safety assessments performed at the time point of withdrawal, are summarized, separately to the planned visits. A P-value <0.05 is taken as significant for all analyses.

Protocol-Required Safety Laboratory Assessment is documented in Table 5.

TABLE 5

| Laboratory Assessments | Parameters | | | |
|---|---|---|---|---|
| Hematology | Platelet count | RBC indices: | | White blood cell |
| | Red blood cell (RBC) Count | MCV | | (WBC) count |
| | Hemoglobin | MCH | | with |
| | Hematocrit | % Reticulocytes | | Differential: Neutrophils Lymphocytes Monocytes Eosinophils Basophils |
| Clinical Chemistry* | Blood urea nitrogen (BUN) | Potassium | Asparatate Aminotransferase (AST)/ Serum Glutamic-Oxaloacetic Transaminase (SGOT) | Total and direct bilirubin |
| | Creatinine | Sodium | Alanine Aminotransferase (ALT)/ Serum Glutamic-Pyruvic Transaminase (SGPT) | Total protein |
| | Glucose (fasting) | Calcium | Alkaline phosphatase | |
| Other Screening Tests | Microbiome analysis of stool samples, infectious agent screening of blood and stool samples of donor and recipient (See Section 4.1, Paragraph Donor Screening) | | | |

Notes:
*if INR measured which may indicate severe liver injury (possible Hy's Law), must be reported as an SAE

Example 2: Vancomycin and Familial Fecal Microbiota Transplant for the Treatment of Subjects with Alzheimer's Disease Objectives: Improve the core features of Alzheimer's Disease and the short and long-term effects of outcomes; Improve the quality of life of subjects and their caregivers; Assess gastrointestinal microbiome relative abundance before and after familial fecal microbiota transplant using whole genome shotgun sequencing Procedure: Participants in the study are required to meet the clinician on fifteen occasions, two appointments for screening and baseline assessment, as well as to receive prescription for vancomycin, one appointment for familial fecal microbiota transplant (FFMT) by colonoscopy and twelve appointments to study sites for the post-trial assessment.

Participants in the study are required to meet the clinician on fifteen occasions, two appointments for screening and baseline assessment, as well as to receive prescription for vancomycin, one appointment for familial fecal microbiota transplant (FFMT) by colonoscopy and twelve appointments to study sites for the post-trial assessment.

Familial Fecal Microbiota Transplantation by Colonoscopy: After the baseline data have been collected and the inclusion and exclusion criteria verified, the patient will be scheduled for familial fecal microbiota transplantation (FFMT) at an outpatient surgical center. This transplant will utilize donor stool from a first degree relative (sibling or child)

The patient will prepare for the procedure the day prior by drinking a prescribed regimen of bowel cleanse solution and water. The patent will present for the procedure having fasted and prepped as instructed by the investigator. The patient will undergo the FFMT procedure under anesthesia and be driven home afterwards. Under no circumstances is the patient to drive themselves home.

Familial Fecal Microbiota Transplant by Enema: After 4 weeks the patient will begin FFMT enemas at home utilizing fresh stool from the same donor as the first FFMT. The patient will lie in the lateral decubitus position and the enema will be inserted into the anus. The fecal material will be slowly expelled into the patient's rectum. The patient will remain in the lateral decubitus position for approximately 30 minutes before getting up. The patient may then use the restroom.

Post Treatment Assessment: After FFMT by colonoscopy the patient will be called for post treatment follow-up visits monthly for the Alzheimer's disease assessments MMSE and Qol AD. The patient will also bring a fresh stool sample for microbiome analysis to these appointments. At the 3-month, 6-month, 9-month, and 12-month follow-up visits the patient will be assessed by following parameters: physical examination, vital signs, Adverse Events, concomitant medications, MMSE and Qol AD. The patient will have blood drawn for laboratory analysis and will bring a fresh stool sample for microbiome analysis. Table 6 documents the treatment protocol.

TABLE 6

| Intervention Name | Vancomycin | Familial Fecal Microbiota Transplant |
|---|---|---|
| Dose Formulation | Suspension of 83 mg/mL (500 mg/6 mL) | Emulsification |
| Route of Administration | Oral | Delivered to the colon directly by colonoscope in the first transplant, and by enema in all subsequent transplants |

Processing of Sample/Dosing: We will treat patients with AD using vancomycin followed by familial fecal microbiota transplant. The vancomycin will be prescribed at the second baseline visit and will be given for 10 days. This is an open-label study, so blinding is not a component. For FFMT the donor provides a fresh stool sample the morning of the procedure. The sample is brought by the donor to the study site for processing. Processing includes emulsification with sterile normal saline at a 1:1 ratio to create a fecal slurry. Following the FFMT by colonoscopy the caregiver is taught how to prepare and administer the FFMT enemas at home (during the week 4 visit).

Statistical Analysis: The statistical evaluation is performed by an outside statistician using SAS® version 9.3 or higher (Statistical Analysis System, SAS Inc., Cary, N.C.) software package. Descriptive summaries are given by treatment group and/or overall. The number of subjects within each treatment group of the analysis set is given in each table. Categorical variables are summarized with counts (n) and percentages (%), together with the number of non-missing values. Fisher's exact test for categorical variables is used. The number of non-missing values is used as the denominator for the calculation of percentages. Incidence of adverse events is based on the number of subjects in the respective analysis set and treatment group. Descriptive statistics for continuous variables are comprised of the number of non-missing observations (n), mean, standard deviation (SD), median, minimum (Mm) and maximum (Max), if not otherwise stated. Student's t-test and Mann-Whitney for continuous parametric and nonparametric variables are used respectively. ANOVA is used for comparing means between individual groups. When applicable, these summaries are provided by visit. In case of premature withdrawal from the trial, efficacy and safety assessments performed at the time point of withdrawal, are summarized, separately to the planned visits. A P-value <0.05 is taken as significant for all analyses.

Protocol-Required Safety Laboratory Assessment is documented in Table 7.

TABLE 7

| Laboratory Assessments | Parameters | | |
|---|---|---|---|
| Hematology | Platelet count Red blood cell (RBC) Count Hemoglobin Hematocrit | RBC Indices: MCV MCH % Reticulocytes | White blood cell (WBC) count with Differential: Neutrophils Lymphocytes Monocytes Eosinophils Basophils |

TABLE 7-continued

| Laboratory Assessments | Parameters | | | |
|---|---|---|---|---|
| Clinical Chemistry* | Blood urea nitrogen (BUN) | Potassium | Asparatate Aminotransferase (AST)/ Serum Glutamic- Oxaloacetic Transaminase (SGOT) | Total and direct bilirubin |
| | Creatinine | Sodium | Alanine Aminotransferase (ALT)/ Serum Glutamic-Pyruvic Transaminase (SGPT) | Total protein |
| | Glucose (fasting) | Calcium | Alkaline phosphatase | |
| Other Screening Tests | Microbiome analysis of stool samples, infectious agent screening of blood and stool samples of donor and recipient (See Section 4.1, Paragraph Donor Screening) | | | |

Notes:
*if INR measured which may indicate severe liver injury (possible Hy's Law), must be reported as an SAE

Example 3: Vancomycin and Familial Fecal Microbiota Transplant for the Treatment of Subjects with Autism Spectrum Disorder Objectives: Improve the core features of Autism Spectrum Disorder (ASD) (social interaction, communication and behavioral problems) as well as the short and long-term effects of the outcomes; Improve other non-core aspects of behavior or function such as self-injurious behavior; Improve the quality of life of subjects and their caregivers; And assess gastrointestinal microbiome relative abundance before and after familial fecal microbiota transplant using whole genome shotgun sequencing.

Procedure: This is an open-label clinical trial to evaluate the benefits of familial fecal microbiota transplant following a 6-week treatment with Vancomycin in minor and adult subjects with ASD for treatment of social deficits and language delays.

Participants in the study are required to meet the clinician on 15 occasions, two appointments for baseline assessment, one appointment for the fecal microbiota transplant procedure by colonoscopy, and twelve appointments to for the post-transplant assessment.

Donor Screening: Once the patient has been deemed eligible and baseline measurements have been collected, a suitable donor will be determined. This donor should be a first-degree relative of the patient (parent, sibling, or child). This donor will present to the clinic for vital signs, physical exam, blood draw for laboratory analysis, and will provide a fresh stool sample for testing. Blood tests will include the following: CBC, complete metabolic profile, CMV IgG, EBV Ab panel, *Entamoeba histolytica* Ab, Hepatitis A Ab, Hepatitis B core Ab, Hepatitis B surface Ab, Hepatitis C Ab, HHV-6 IgG, HIV antibody, HSV 1 & 2 IgG, HTLV-I/II Ab, IgE, immunoglobulins panel QT IgM, IgG, IgA, JC virus Ab. Lymphocyte subset panel I, *Strongyloides stercoralis*, and Syphilis serology. Stool tests will include: CRE, ESBLs, GI panel by PCR, *H. pylori*, and VRE.

Processing of Sample/Dosing: We will treat minors and adults with ASD using vancomycine followed by familial fecal microbiota transplant. The vancomycin will be prescribed at the second baseline visit and will be given for six weeks. This is an open-label study, so blinding is not a component. For FFMT the donor will provide a fresh stool sample the morning of the procedure. This will be brought by the donor to the study site for processing. Processing includes emulsification with sterile normal saline at a 1:1 ratio to create a fecal slurry. Following the FFMT by colonoscopy the caregiver will be taught how to prepare and administer the FFMT enemas at home (during the week 4 visit).

Vancomycin Treatment: Patient will be given a course of vancomycin of 6-week duration. The dose will 250 mg of liquid suspension (formulated in a concentration of 500 mg/6 mL) every 8 hours.

Familial Fecal Microbiota Transplantation by Colonoscopy: The patient will be scheduled for familial fecal microbiota transplantation (FFMT) at an outpatient surgical center, to be conducted the day after completion of the Vancomycin treatment. The patient will prepare for the procedure the day prior by drinking a prescribed regimen of bowel cleanse solution and water. The patent will present for the procedure having fasted and prepped as instructed by the investigator. The patient will undergo the FFMT procedure under anesthesia and be driven home afterwards. Under no circumstances is the patient to drive themselves home.

Familial Fecal Microbiota Transplant by Enema: After 4 weeks the patient will begin FFMT enemas at home utilizing fresh stool from the same donor as the first FFMT. The patient will lie in the lateral decubitus position and the enema will be inserted into the anus. The fecal material will be slowly expelled into the patient's rectum. The patient will remain in the lateral decubitus position for approximately 30 minutes before getting up. The patient may then use the restroom.

Post Treatment Assessment: After FFMT, the patient will be called for monthly post treatment follow-up visits. The patient will bring a fresh stool sample for microbiome testing to each of these visits. The following tests will be administered at these monthly visits: ATEC, CARS-II, CFQL and SRS-II. During the 3, 6, 9, and 12-month follow-up visits the patient will have blood drawn for complete blood count and metabolic panel. Vital signs will be taken, adverse events discussed, and concomitant medications will be updated. At the week 4 visit the patient's family will be shown how to prepare and administer the FFMT by enema. During weeks in which the patient does not have a visit, a phone call will be made to check on the patient, and, starting during week 4, to remind the caregiver to administer the FFMT enema at home).

Table 8 documents the treatment protocol.

TABLE 8

| Intervention Name | Vancomycin | Familial Fecai Microbiota Transplant |
|---|---|---|
| Dose Formulation | Suspension of 83 mg/mL (500 mg/6 mL) | Emulsification |
| Route of Administration | Oral | Delivered to the colon directly by colonoscope in the first transplant, and by enema in all subsequent transplants |

Statistical Analysis. The statistical evaluation is performed by an outside statistician using SAS® version 9.3 or higher (Statistical Analysis System, SAS Inc., Cary, N.C.) software package. Descriptive summaries are given by treatment group and/or overall. The number of subjects within each treatment group of the analysis set is given in each table. Categorical variables are summarized with counts (n) and percentages (%), together with the number of non-missing values. Fisher's exact test for categorical variables is used. The number of non-missing values is used as the denominator for the calculation of percentages. Incidence of adverse events is based on the number of subjects in the respective analysis set and treatment group. Descriptive statistics for continuous variables are comprised of the number of non-missing observations (n), mean, standard deviation (SD), median, minimum (Min) and maximum (Max), if not otherwise stated. Student's t-test and Mann-Whitney for continuous parametric and nonparametric variables are used respectively. ANOVA is used for comparing means between individual groups. When applicable, these summaries are provided by visit. In case of premature withdrawal from the trial, efficacy and safety assessments performed at the time point of withdrawal, are summarized, separately to the planned visits. A P-value <0.05 is taken as significant for all analyses.

Example 4: Treatment of Over 300 Patients with Familial Fecal Microbiota Transplant Procedure: Over 300 patients were treated with familial fecal microbiota transplant via the methods outlined above. If the fecal donor member was compatible with the patient, treatment of the patient was successful.

Results: Out of over 300 patients treated, two patients had Rheumatoid arthritis that was healed, one patient had Alzheimer's that improved, two patients had Crohn's disease that improved, and two patients had psoriasis that improved.

Example 5: Presence of the SARS-CoV-2 by NGS of Fecal Samples

Objective: In view of the large percentage of SARS-CoV-2 detectible by RT-PCR in stools of infected patients, the objective was to identify the presence of the SARS-CoV-2 by NGS of fecal samples from symptomatic study participants positive for SARS-CoV-2 by nasopharyngeal sample RT-PCR, in addition to asymptomatic individuals (with or without prior nasopharyngeal sample RT-PCR). The objective was also to execute whole genome analysis to characterize SARS-CoV-2 mutational variations to identify potentially significant nucleotide changes.

Procedure: Study participants (n=14) underwent testing for SARS-CoV-2 from fecal samples by whole genome enrichment NGS. Following fecal collection (Zymo Research Shield Fecal Collection Tubes), RNA was extracted (Qiagen Allprep Power Viral Kit), reverse transcribed (New England Biolabs NEBNext 1st and 2nd Strand Synthesis Modules), library prepped (Illumina Nextera Flex for Enrichment), enriched (Illumina Respiratory Virus Oligo Panel), and sequenced on Illumina's NextSeq 550 System. Sequences were then mapped to the SARS-CoV-2 Wuhan-Hu-1 (MN90847.3) complete genome utilizing One Codex's SARS-CoV-2 bioinformatics analysis pipeline. SARS-CoV-2 positive samples were further analyzed for mutational variants that differed from the reference genome. Of the 14 study participants, 12 also had their nasopharyngeal swabs tested for SARS-CoV-2 by RT-PCR.

Results: The results from patients that had their stool samples tested by whole genome enrichment NGS, and their nasopharyngeal swabs tested by RT-PCR for the presence of SARS-CoV-2 were evaluated. Of the 14 study participants, ten were symptomatic and tested positive for SARS-CoV-2 by RT-PCR, two asymptomatic individuals tested negative, and two other asymptomatic individuals did not undergo RT-PCR testing (Table 34). Patients 5 and 7, which tested positive by RT-PCR from nasopharyngeal swabs, were treated with the protocol from Example 5 above (Hydroxychloroquine, Azithromycin, vitamin C, vitamin D, and zinc for 10 days prior to fecal collection). Similarly, after positive nasopharyngeal swab, patient 13 was treated with vitamin C, vitamin D, and zinc for 10 days (the same protocol as noted above in Example 5) before fecal collection. The concordance of SARS-CoV-2 detection by enrichment NGS from stools among positive non-treated patients tested by RT-PCR nasopharyngeal analysis was 100% (7/7). Patient 8, who did not undergo nasopharyngeal analysis, tested positive for SARS-CoV-2 by NGS. The three patients (5, 7, 13) that received treatment prior to providing fecal samples, all tested negative by NGS. Asymptomatic patients 2 and 9, who tested negative by nasopharyngeal swab, were also negative by NGS, as was asymptomatic patient 14. Table 9 outlines the symptoms and SARS-CoV-2 testing results.

TABLE 9

| Sample ID | Symptoms | Nasopharyngeal Swab (RT-PCR) | Treated | Fecal (NGS) | Patient Location |
|---|---|---|---|---|---|
| Patient 1 | febrile, diarrhea, anosmia, O2 sat. <90% | + | no | + | PA |
| Patient 3 | febrile, diarrhea, O2 sat. <90% | + | no | + | CA |
| Patient 4 | febrile, diarrhea, anosmia, O2 sat. <90% | + | no | + | AZ |
| Patient 6 | febrile, cough, anosmia | + | no | + | AZ |
| Patient 8 | none | n/a | no | + | CA |
| Patient 10 | febrile, cough, headache | + | no | + | GA |
| Patient 11 | febrile, cough, headache | + | no | + | GA |

TABLE 9-continued

| Sample ID | Symptoms | Nasopharyngeal Swab (RT-PCR) | Treated | Fecal (NGS) | Patient Location |
|---|---|---|---|---|---|
| Patient 12 | febrile, cough | + | no | + | GA |
| Patient 5 | febrile, cough | + | yes | − | CA |
| Patient 7 | febrile, cough | + | yes | − | GA |
| Patient 13 | febrile, cough | + | yes | − | GA |
| Patient 2 | none | − | no | − | CA |
| Patient 9 | none | − | no | − | CA |
| Patient 14 | none | n/a | no | − | CA |

All fecal samples analyzed by enrichment NGS from positive patients by RT-PCR, achieved 100% genome coverage of SARS-CoV-2 except for patient 3 which had 45%, and patient 10 which had 93% coverage. Table 10 outlines the enrichment NGS metrics.

TABLE 10

| Sample ID | Genome Coverage | # Variants (over 10x) | Mapped Reads | Mean Depth |
|---|---|---|---|---|
| Patient 1 | 100% | 11 | 465645 | 1129.8x |
| Patient 3 | 45% | 11 | 5984 | 31.7x |
| Patient 4 | 100% | 9 | 131582 | 318.6x |
| Patient 6 | 100% | 10 | 793603 | 1924.6x |
| Patient 8 | 100% | 10 | 496852 | 1206.7 |
| Patient 10 | 93% | 9 | 5929 | 15.6x |
| Patient 11 | 100% | 10 | 1270734 | 3075.3x |
| Patient 12 | 100% | 10 | 38256 | 92.7x |

The total number of SARS-CoV-2 mapped reads for patients 1, 3, 4, 6, 8, 10, 11, and 12 were 465645, 5984, 131582, 793603, 496852, 5929, 1270734, and 38256 respectively. The mean read depths of SARS-CoV-2 for patients 1, 3, 4, 6, 8, 10, 11, and 12 were 1129.8x, 31.7x, 318.6x, 1924.6x, 1206.7x, 15.5x, 3075.3x, and 92.7x, and respectively. The read depths at specific coordinates along the SARS-CoV-2 genome for each patient are captured in FIGS. 3A-3H. Whole genome alignment of SARS-CoV-2 in patients 1, 3, 4, 6, 8, 10, 11, and 12 (respectively) as identified by One Codex's SARS-CoV-2 analysis pipeline. The x-axis depicts the genomic coordinates as aligned to the MN908947.3 reference genome, and the y-axis represents the read depth at specific loci.

Following alignment and mapping of SARS-CoV-2, patient genomes were compared to the Wuhan-Hu-1 (MN90847.3) SARS-CoV-2 reference genome via One Codex's bioinformatics pipeline to identify mutational variations. This analysis identified nucleotide variants at positions nt241 (C→T) and nt23403 (A→G) across all positive patients, and variants at positions nt3037 (C→T) and nt25563 (G→T) in seven of the eight patients (Table 3). Interestingly, patients 8, 11, and 12 harbored the same set of variants, as did patients 4 and 6 (who were kindred). Unique variants not identified in any of the other individuals were detected in patients 1, 3, 6, and 10, with patient 3 harboring the most distinct SARS-CoV-2 genome with eight unique variants, followed by patient I with seven. Collectively, there were thirty-three different mutations among the patients in which SARS-CoV-2 was detected by whole genome enrichment NGS. Table 11 outlines the SARS-CoV-2 genomic positions, variant changes, and frequencies across the positive patient cohort.

TABLE 11

| Region (ORF) | Position | Variant | Patient 1 | Patient 3 | Patient 4 | Patient 6 | Patient 8 | Patient 10 | Patient 11 | Patient 12 |
|---|---|---|---|---|---|---|---|---|---|---|
| 5'-UTR | 241 | C → T | 100% | 100% | 100% | 100% | 100% | 100% | 100% | 100% |
| 1a | 833 | T → C | x | x | x | x | 100% | x | 100% | 100% |
| 1a | 1059 | C → T | x | x | 100% | 100% | 99% | 100% | 100% | 100% |
| 1a | 1758 | C → T | x | x | 100% | 100% | x | x | x | x |
| 1a | 1973 | C → T | x | x | x | 87% | x | x | x | x |
| 1a | 3037 | C → T | 100% | x | 100% | 100% | 100% | 100% | 100% | 100% |
| 1a | 3078 | C → T | x | 89% | x | x | x | x | x | x |
| 1a | 4866 | G → T | 75% | x | x | x | x | x | x | x |
| 1a | 6720 | C → T | 93% | x | x | x | x | x | x | x |
| 1a | 8102 | G → T | x | 100% | x | x | x | x | x | x |
| 1a | 9401 | T → C | x | x | x | x | x | 64% | x | x |
| 1a | 9403 | T → A | x | x | x | x | x | 64% | x | x |
| 1a | 10870 | G → T | x | x | 100% | 100% | x | x | x | x |
| 1a | 11123 | G → A | x | x | 100% | 100% | x | x | x | x |
| 1b | 14408 | C → T | 100% | x | 100% | 100% | 100% | x | 100% | 100% |
| 1b | 14877 | C → T | x | 100% | x | x | x | x | x | x |
| 1b | 16616 | C → T | x | x | x | x | 100% | x | 100% | 100% |
| 1b | 16848 | C → T | 100% | x | x | x | x | x | x | x |
| 1b | 18652 | C → A | x | x | x | x | x | 83% | x | x |
| 1b | 19989 | T → G | x | 100% | x | x | x | x | x | x |
| Spike | 21576 | T → G | x | 83% | x | x | x | x | x | x |
| Spike | 23264 | G → A | x | 75% | x | x | x | x | x | x |
| Spike | 23403 | A → G | 100% | 100% | 100% | 100% | 100% | 100% | 100% | 100% |
| Spike | 23603 | C → T | 82% | x | x | x | x | x | x | x |
| 3a | 25563 | G → T | x | 100% | 100% | 100% | 100% | 100% | 100% | 100% |
| 3a | 25976 | C → A | x | x | x | x | x | x | 100% | 100% |
| 8 | 27964 | C → T | x | x | x | x | 100% | x | 100% | 100% |
| Nucleoprotein | 28881 | G → A | 100% | x | x | x | x | x | x | x |

TABLE 11-continued

| Region (ORF) | Position | Variant | Patient 1 | Patient 3 | Patient 4 | Patient 6 | Patient 8 | Patient 10 | Patient 11 | Patient 12 |
|---|---|---|---|---|---|---|---|---|---|---|
| Nucleoprotein | 28882 | G → A | 100% | x | x | x | x | x | x | x |
| Nucleoprotein | 28883 | G → C | 100% | x | x | x | x | x | x | x |
| Nucleoprotein | 28997 | C → T | x | 100% | x | x | x | x | x | x |
| Nucleoprotein | 29019 | A → T | x | 100% | x | x | x | x | x | x |
| Nucleoprotein | 29364 | C → G | x | x | x | x | x | 85% | x | x |

Discussion; Although previous studies have identified SARS-CoV-2 in fecal collections by RT-PCR, this study was able to report w % bole genome sequencing (WGS) of SARS-CoV-2 from stool samples. SARS-CoV-2 was identified in patients that tested positive by nasopharyngeal swab RT-PCR analysis and unique genomes in 62.5% of the NGS positive patients was observed. The overall homology among the genomes was high (99.97%), with variations identified in the ORF regions 1a, 1b, S, 3a, 8, and N. Of particular interest, was the adenine to guanine change in the S protein at position nt23403 which converts aspartic acid to glycine (D→G).

Conclusion: Next generation sequencing identified the SARS-CoV-2 whole genome sequence in 100% of patients with positive nasopharyngeal RT-PCR and did not detect it in treated patients, or those with negative rt-PCR. These results highlight the importance of metagenomic analysis of the SARS-CoV-2 viral genome.

Example 6: Study of Microbiome of Patients with COVID Versus Patients without COVID 36 Covid-19 patients were studied in a cross-sectional study with 14 healthy controls (HC) to identify microbiome diversity by whole genome enrichment NGS. Patient records were included and compared any significant changes on species, genus, family, order, class, and phylum levels of the Covid-19 positive and HC population.

Deep shotgun microbiome sequencing analysis was performed on fecal samples from the 36 Covid-19 positive patients by whole genome enrichment NGS. The observed versus expected rates were primarily reported.

All individuals aged 3 years and older were eligible for inclusion. For each patient, a so-called period of eligibility for study inclusion was defined, which commenced on the latest of the study start date; A patient's period of eligibility ended on the earliest of registration termination; the end of data collection from their practice; or death.

Data Analysis

The differential taxa was conducted between the Gastrointestinal Microbiome of Covid-19 positive and HC relative abundance utilizing One Codex's bioinformatics analysis pipeline. For evaluating any statistical significance of the patient's data at each Classification at phylum, class, order, family, and genus levels, a Fisher's exact test was conducted between the two variables. Statistical analysis was conducted using chi-squared statistics by R version 3.6.1 (2019-07-05). In the statistical analysis, p-value, Confidence interval and Odds ratio were considered for all comparisons.

Results

The study population included 50 patients (36 Covid-19 positives and 14 HC). For the HC population, data from patients after December 2019 were excluded from the study to avoid overlap between any Covid-19 possible positive patients.

The results from the 50 total patients that had their stool samples tested by whole genome enrichment NGS was evaluated. Detailed demographic and summary data, clinical characteristics including total numbers of diagnoses and events were analyzed for the study cohorts, and are included in Table 12.

TABLE 12

| No | Age | Sex | Significant Past Medical History | PCR Date | Covid-19 PCR Results | Stool Collection Date | Sx Severity at BL |
|---|---|---|---|---|---|---|---|
| 1 | 20 | Female | Hypothyroid, Hashimoto, LCH | Jul. 10, 2020 | Positive | Jun. 24, 2020 | Severe |
| 2 | 21 | Female | Nothing to report | No info | Positive | Apr. 5, 2020 | Moderate |
| 3 | 56 | Male | Nothing to report | No info | Positive | Apr. 5, 2020 | No Info |
| 4 | 25 | Female | Asthma, Renux, GI issue | No info | Positive | Mar. 29, 2020 | Mild |
| 5 | 25 | Female | No info | No info | Positive | No info | Moderate |
| 6 | 44 | Female | Food sensitivities, gut issues | Apr. 8, 2020 | Positive | Apr. 13, 2020 | Severe |
| 7 | No info | | No info | No info | Positive | No info | No info |
| 8 | 53 | Male | No info | No info | Positive | No info | Severe |
| 9 | 23 | Male | No info | No info | Positive | No info | No info |
| 10 | 19 | Male | Nothing to report | Apr. 22, 2020 | Positive | May 6, 2020 | No info |
| 11 | 35 | Female | Seizure | No info | Positive | Jun. 23, 2020 | No info |
| 12 | 32 | Male | Nothing to report | Positive | | Jun. 26, 2020 | Mild |
| 13 | 63 | Female | No info | No Info | Positive | Jul. 20, 2020 | No info |
| 14 | No info | Male | No info | No info | Positive | Jun. 28, 2020 | No info |

TABLE 12-continued

| No | Age | Sex | Significant Past Medical History | PCR Date | Covid-19 PCR Results | Stool Collection Date | Sx Severity at BL |
|---|---|---|---|---|---|---|---|
| 15 | 61 | Male | Nothing to report | No info | Positive | No info | No info |
| 16 | 50+ | Male | No info | No Info | Positive | No info | No info |
| 17 | 43 | Female | No info | No info | Positive | No info | Severe |
| 18 | No info | Female | No info | No info | Positive | Jul. 27, 2020 | No info |
| 19 | 70 | Male | No info | No info | Positive | Aug. 5, 2020 | Severe |
| 20 | 56 | Male | Nothing to report | No info | Positive | Aug. 10, 2020 | Severe |
| 21 | 50+ | Male | No info | No info | Positive | No info | Moderate |
| 22 | 59 | Female | No info | No info | Positive | Sep. 4, 2020 | Severe |
| 23 | 35 | Female | No info | No info | Positive | No info | Moderate |
| 24 | 71 | Male | No info | No info | Positive | No info | No info |
| 25 | 58 | Female | No info | No info | Positive | No info | Moderate |
| 26 | 61 | Female | No info | No info | Positive | No info | No info |
| 27 | 55 | Male | Nothing to report | Positive | | Oct. 21, 2020 | Severe |
| 28 | 66 | Female | No info | No info | Positive | No info | Moderate |
| 29 | No info | No info | No info | No info | Positive | No info | No info |
| 30 | 66 | Female | No info | No info | Positive | No info | Severe |
| 31 | No info | No info | No info | No info | Positive | No info | No info |
| 32 | 61 | Female | No info | No info | Positive | No info | Severe |
| 33 | 69 | Male | No info | No info | Positive | No info | No info |
| 34 | No info | No info | No info | No info | Positive | No info | No info |
| 35 | 40 | Female | No info | No info | Positive | No info | Moderate |
| 36 | No info | No info | No info | No info | Positive | No info | No info |
| 37 | 6 | Male | Nothing to report | Not applicable | Not applicable-Negative | No info | Not applicable-Negative |
| 38 | 6 | Female | Nothing to report | Not applicable | Not applicable-Negative | No info | Not applicable-Negative |
| 39 | 8 | Female | Nothing to report | Not applicable | Not applicable-Negative | No info | Not applicable-Negative |
| 40 | 3 | Female | Nothing to report | Not applicable | Not applicable-Negative | No info | Not applicable-Negative |
| 41 | 11 | Male | Nothing to report | Not applicable | Not applicable-Negative | No info | Not applicable-Negative |
| 42 | 3 | Male | Nothing to report | Not applicable | Not applicable-Negative | No info | Not applicable-Negative |
| 43 | 4 | Female | Nothing to report | Not applicable | Not applicable-Negative | No info | Not applicable-Negative |
| 44 | 7 | Female | Nothing to report | Not applicable | Not applicable-Negative | No info | Not applicable-Negative |
| 45 | 16 | Female | Nothing to report | Not applicable | Not applicable-Negative | No info | Not applicable-Negative |
| 46 | 9 | Male | Nothing to report | Not applicable | Not applicable-Negative | No info | Not applicable-Negative |
| 47 | 10 | Female | Nothing to report | Not applicable | Not applicable-Negative | No info | Not applicable-Negative |
| 48 | 7 | Female | Nothing to report | Not applicable | Not applicable-Negative | No info | Not applicable-Negative |
| 49 | 55 | Female | Nothing to report | Not applicable | Not applicable-Negative | No info | Not applicable-Negative |
| 50 | 17 | Female | Nothing to report | Not applicable | Not applicable-Negative | No info | Not applicable-Negative |

Tables 13-18 demonstrate the association between relative abundance of the gastrointestinal microbiome at Phylum, Class, Order, Family and Species level of Covid-19 positive (Covid+) vs. healthy control (Covid−) patients. A 95% Confidence interval (CI) and odds ratio (OR) were used in addition to the p-value for better comparison.

TABLE 13

| Classification Phylum | Covid + Patients Presence | Covid + Patients Absence | Covid − Patients Presence | Covid − Patients Absence | Statistical ($P < 0.05$) Significance | Fisher exact test value Intervals(CI) and odds ratio(OR) with 95% Confidence |
|---|---|---|---|---|---|---|
| Actinobacteria | 31 | 5 | 14 | 0 | Yes* | $P < 0.00001$(CI; 0.00-0.3, OR = 0) |
| Firmicutes | 36 | 0 | 14 | 0 | No** | p-value 1 |
| Proteobacteria | 33 | 3 | 14 | 0 | Yes | P value 0.003(CI; 0.00-0.48, OR = 0) |
| Bacteroidetes | 36 | 0 | 14 | 0 | No | p-value 1 |

TABLE 14

| Classification Class | Covid + Patients Presence | Covid + Patients Absence | Covid − Patients Presence | Covid − Patients Absence | Statisical Significance ($P < 0.05$) | Fisher exact test value with 95% Confidence Intervals (CI) and odds ratio(OR) |
|---|---|---|---|---|---|---|
| Actinobacteria | 24 | 12 | 14 | 0 | Yes | $P < 0.00001$(CI; 0.00-0.07, OR = 0) |
| Clostridia | 36 | 0 | 14 | 0 | No | p-value 1 |
| Negativicutes | 30 | 6 | 14 | 0 | Yes | $P < 0.00001$(CI; 0.00-0.21, OR = 0) |
| Betaproteobacteria | 21 | 15 | 12 | 2 | Yes | $P < 0.00001$(CI; 0.10-0.46, OR 0.22) |
| Bacteroidia | 36 | 0 | 14 | 0 | No | p-value 1 |
| Gammaproteobacteria | 21 | 15 | 9 | 5 | No | p-value 0.46(CI; 0.4-1.4, OR = 0.77) |
| Erysipelotrichia | 33 | 3 | 11 | 3 | Yes | p-value 0.009(CI; 01.27-8.77, OR = 3.19) |

TABLE 15

| Classification Order | Covid + Patients Presence | Covid + Patients Absence | Covid − Patients Presence | Covid − Patients Absence | Statistical ($P < 0.05$) Significance | Fisher exact test Confidence Intervals(CI) and odds ratio(OR) value with 95% |
|---|---|---|---|---|---|---|
| Bifidobacteriales | 20 | 16 | 14 | 0 | Yes | $P < 0.00001$ (CI; 0.00-0.05, OR = 0) |
| Clostridiales | 36 | 0 | 14 | 0 | No | p-value 1 |
| Veillonellales | 14 | 22 | 11 | 3 | Yes | $P < 0.00001$ (CI; 0.08-0.30, OR = 0.16) |
| Burkholderiales | 21 | 15 | 12 | 2 | Yes | $P < 0.00001$ (CI; 0.11-0.50, OR = 0.24) |
| Bacteroidales | 36 | 0 | 14 | 0 | No | p-value 1 |
| Erysipelotrichales | 33 | 3 | 14 | 0 | Yes | 6.603 (CI; 0.00-0.48, OR = 0) |
| Enterobacterales | 21 | 15 | 6 | 8 | Yes | p-value 0.03 (CI; 01.04-3.47, OR = 3.90) |

TABLE 16

| Classification | Covid + Patients | | Covid − Patients | | Statistical Significance (P < 0.05) | Fisher exact test Confidence Intervals(CI) and odds ratio(OR) value with 95% |
|---|---|---|---|---|---|---|
| Family | Presence | Absence | Presence | Absence | | |
| Bifidobacteriacae | 20 | 16 | 14 | 0 | Yes | P < 0.00001 (CI; 0.00-0.05, OR = 0) |
| Clostridiacae | 35 | 1 | 14 | 0 | No | p-value 0.24 (CI; 0.0-2.4, OR = 0) |
| Veilloneacellae | 15 | 22 | 11 | 3 | Yes | P < 0.00001(CI; 0.05-0.25, OR = 0.12) |
| Ruminococcacea | 36 | 0 | 14 | 0 | No | p-value 1 |
| Sutterellacae | 19 | 17 | 11 | 3 | Yes | p-value 0.0003(CI; 0.16-20.61, OR = 0.32) |
| Faecalibacterium | 31 | 5 | 14 | 0 | Yes | p-value 0.00007(CI; 0.00-0.27, OR = 0) |
| Prevotellaceae | 17 | 19 | 10 | 4 | Yes | p-value 0.0009(0; 0.19-0.67, OR = 0.36) |
| Erysipelotrichaceae | 33 | 3 | 14 | 0 | Yes | p-value 0.006(CI; 0.00-0.57, OR = 0) |
| Entero-bacteriaceae | 21 | 15 | 8 | 6 | No | p-value 1 |

TABLE 17

| Classification | Covid + Patients | | Covid − Patients | | Statistical Significance | Fisher exact test value |
|---|---|---|---|---|---|---|
| Genus | Presence | Absence | Presence | Absence | (P < 0.05) | |
| *Bifidobacterium* | 20 | 16 | 14 | 0 | Yes | P < 0.00001(CI; 0.00-0.05, OR = 0) |
| *Clostridium* | 33 | 3 | 14 | 0 | Yes | p-value 0.006(CI; 0.00-0.57, OR = 0) |
| *Veillonella* | 14 | 22 | 11 | 3 | Yes | P < 0.00001(CI; 0.08-0.30 0R = 0.16) |
| *Ruminococcus* | 30 | 6 | 14 | 0 | Yes | p-value 0.00007(CI; 0.00-0.21, OR=0) |
| *Sutterella* | 7 | 29 | 12 | 2 | Yes | P <0.00001(CI; 0.01-0.08 OR = 0.03) |
| *Faecalibacterium* | 31 | 5 | 14 | 0 | Yes | p-value 0.00007(CI; 0.00-0.21, OR = 0) |
| *Prevotella* | 10 | 26 | 3 | 11 | No | p-value 0.40(CI; 0.68-2.83, OR = 1.38) |
| *Erysiplato-Clostridium* | 26 | 10 | 12 | 2 | Yes | p-value 0.03(CI; 0.20-0.96, OR = 0.45) |
| *Escherichia* | 21 | 15 | 7 | 7 | No | p-value 0.32(CI; 0.76-2.5, OR = 1.37) |
| *Klebsiella* | 5 | 33 | 1 | 13 | No | p-value 1 |

Table 18

| Classification | Covid + Patients | | Covid − Patients | | Statistical Significance | Fisher exact test value |
|---|---|---|---|---|---|---|
| Species | Presence | Absence | Presence | Absence | (P < 0.05) | |
| *Bifidobacterium* | 20 | 16 | 14 | 0 | Yes | P < 0.00001 (CI; 0.00-0.05, OR = 0) |
| *Clostridium* | 33 | 3 | 14 | 0 | Yes | p-value 0.006(CI; 0.00-0.57, OR = 0) |
| *Veillonella* | 14 | 22 | 11 | 3 | Yes | P <0.00001 (CI 0.08-0.30 OR = 0.16) |
| *Ruminococcus* | 30 | 6 | 14 | 0 | Yes | p-value 0.00007(CI; 0.00-0.21, OR = 0) |
| *Sutterella* | 7 | 29 | 12 | 2 | Yes | P < 0.00001 (CI; 0.01-0.08 OR = 0.03) |
| *Prevotella* | 10 | 26 | 3 | 11 | No | p-value 0.40 (CI; 0.68-2.83, OR = 1.38) |

Table 18-continued

| Classification | Covid + Patients | | Covid − Patients | | Statistical Significance | |
|---|---|---|---|---|---|---|
| Species | Presence | Absence | Presence | Absence | (P < 0.05) | Fisher exact test value |
| *Erysiplatoclostridium* | 26 | 10 | 12 | 2 | Yes | p-value 0.03 (CI; 0.20-0.96, OR = 0.45) |
| *Escherichia coli* | 21 | 15 | 7 | 7 | No | p-value 0.32 (CI; 0.76-2.5, OR = 1.37) |
| *Klebsiella* | 3 | 33 | 1 | 13 | No | p-value 1 |

According to Tables 13-18, in the 50 patients tested in this study, the relative abundance of Actinobacteria P<0.0001 (CI; 0.00-0.3, OR=0) and Proteobacteria bacteria phyla p-value 0.003 (CI; 0.00-0.48, OR=0) were significantly less than HC. Although there was not any significant dysbiosis in both Bacteroidetes and Firmicutes phyla. At the class level, there was a significant reduction in Actinobacteria P<0.00001 (CI; 0.00-0.07, OR=0), Negativicutes P<0.00001 (CI; 0.00-0.21, OR=0), Betaproteobacteria P<0.00001 (CI; 0.10-0.46, OR=0.22) and Erysipelotrichia p-value 0.009 (CI; 01.27-8.77, OR=3.19).

At the order level, there were significant reductions in more bacteria, including, Bifidobacteriales P<0.00001 (CI; 0.00-0.05, OR=0), Veillonellales P<0.00001 (CI; 0.08-0.30, OR=0.16), Burkholderiales P<0.00001 (CI; 0.11-0.50, OR=0.24), and Erysipelotrichales 0.003 (CI; 0.00-0.48, OR=0) and significant increase in Enterobacterales p-value 0.03 (CI; 01.04-3.47, OR=3.90) compare to the HC.

At the family levels, Bifidobacteriacae P<0.00001 (CI; 0.00-0.05, OR=0), Veilloneacellae P<0.00001 (CI; 0.05-0.25, OR=0.12), Sutterellacae p-value 0.0003 (CI; 0.16-20.61, OR=0.32), *Faecalibacterium* p-value 0.00007 (CI; 0.00-0.27, OR=0), Prevotellaceae p-value 0.0009 (CI; 0.19-0.67, OR=0.36) and Erysipelotrichaceae p-value 0.006 (CI; 0.00-0.57, OR=0) showed a significant reduction in Covid-19 patients compare to the HC.

At the genus level, significant reductions in relative abundances of *Bifidobacterium* P<0.00001 (CI; 0.00-0.05, OR=0), *Clostridium* p-value 0.006 (CI; 0.00-0.57, OR=0), *Veillonella* P<0.00001 (CI; 0.08-0.30 OR=0.16), *Ruminococcus* p-value 0.00007 (CI; 0.00-0.21, OR=0), *Sutterella* P<0.00001 (CI; 0.01-0.08 OR=0.03), *Faecalibacterium* p-value 0.00007 (CI; 0.00-0.21, OR=0) and *Erysiplatoclostridium* p-value 0.03 (CI; 0.20-0.96, OR=0.45) and *Veillonella* P<0.00001 (CI; 0.08-0.30 OR=0.16), were observed.

Findings

Significant alterations of the fecal microbiota was observed, in some cases, for the first time, with special baseline characteristics in Covid-19 positive patients. Except for a significantly higher relative abundance of Enterobacterales at order level in Covid-19 positive patients, there was a significant relative abundance reduction in *Bifidobactenum, Clostridium, Veillonella, Ruminococcus, Sutterella, Faecalibacternum, Erysiplatoclostridium,* and *Veillonella* at the species and genus levels, Bifidobacteriacae, Veilloneacellae, Sutterellacae, Prevotellaceae and Erysipelotrichaceae at the family level, Bifidobacteriales, Veillonellales, Burkholderiales, and Erysipelotrichales at the order level, Actinobacteria, Negativicutes, Betaproteobacteria, and Erysipelotrichia class level and more importantly, Proteobacteria and Actinobacteria at the phylum level.

There were significant reductions in species, genus, family, order, class, and phylum level between Covid-19 positive patients and the control population. Dysbiosis was largest for Actinobacteria and Proteobacteria, at the phylum level, in the Covid-19 positive populations and must be addressed accordingly. The only significant abundance noted was at Enterobacterales order. At the class level, a significant reduction in Actinobacteria. Negativicutes & Betaproteobacteria was observed. At the order level, significant reductions in more bacteria, including, Bifidobacteriales, Veillonellales, Burkholderiales, and Erysipelotrichales, were observed. At the family levels, Bifidobacteriacae, Veilloneacellae, Sutterellacae, *Faecalibacterium*, Erysipelotrichales and Prevotellaceae showed a significant reduction in Covid-19 patients compared to the HC. At the genus level, significant reductions in relative abundances of *Bifidobacterium, Clostridium, Veillonella, Ruminococcus, Sutterella, Faecalibacterium,* and *Erysiplatoclostridium* were observed.

Interpretation

Covid-19 positive patients will have a considerable reduction in microbiota composition and baseline microbiome dysbiosis, levels of cytokines, and inflammatory markers. Addressing the effects of microbial diversity and consequently, suppression of the immunologic response (known as the cytokine storm) is key to prevent and treat the disease. The importance of reduction at the phylum level must be considered as a possibility of an important indicator for Covid-19 positive susceptible patients. Application of diet-based improvement of microbiome would also be considered as an important preventive measure.

Having thus described the invention, it should be apparent that numerous structural modifications and adaptations may be resorted to without departing from the scope and fair meaning of the instant invention as set forth herein above and described herein below by the claims.

What is claimed is:

1. A method of treating COVID-19 infection in an individual, the method comprising the steps of:
   a) screening the individual to determine whether the individual is infected with COVID-19;
   b) preparing an infected individual for a fecal microbiota transplant by directing discontinuation of any existing antibiotic treatment;
   c) preparing the infected individual for the fecal microbiota transplant by directing discontinuation of any existing probiotic treatment except active culture yogurt;
   d) anaerobically acquiring a fecal sample from the infected individual, wherein the fecal sample contains a microbiome of the infected individual;
   e) anaerobically processing the fecal samples from the infected individual by extracting and purifying DNA from the fecal sample of the infected individual and preparing a DNA library of the microbiome of the infected individual;

f) preparing a plurality of donors for the fecal microbiota transplant by directing discontinuation of any existing antibiotic treatment;

g) preparing the plurality of donors for the fecal microbiota transplant by directing discontinuation of any existing probiotic treatment except active culture yogurt;

h) anaerobically acquiring fecal samples from the plurality of donors, wherein the fecal samples of the plurality of donors contain a microbiome of the respective donor;

i) anaerobically processing the fecal samples from the plurality of donors to by extracting and purifying DNA from the fecal samples of the donor and preparing a separate DNA library of the microbiomes of each donor;

j) comparing the DNA library from the infected individual to the DNA library of each donor to determine a matching donor having a DNA library that is more similar to the DNA library of the infected individual as compared to the DNA library of other donors in the plurality of donors;

k) administering rectally into the infected individual a probiotic containing at least one of the following microorganisms to the individual: *Bifidobacterium, Clostridium, Veillonella, Ruminococcus, Faecalibacterium,* and *Sutterella,* wherein the probiotic is derived from the matching donor, wherein the probiotic treats COVID-19 infection in the infected individual.

2. The method of claim 1, wherein step k) comprises administering the probiotic via at least one suppository.

3. The method of claim 2, wherein the suppository is in the form of a liquid dosage, a solid dosage, or a semi-solid dosage.

4. The method of claim 1, wherein the step of administering the probiotic comprises administering the probiotic in one or more of the following forms of administration: fecal transplant or suppository.

5. The method of claim 1, wherein the probiotic administered in step k) is *Clostridium*.

6. The method of claim 1, wherein the probiotic administered in step k) is *Veillonella*.

7. The method of claim 1, wherein the probiotic administered in step k) is *Ruminococcus*.

8. The method of claim 1, wherein the probiotic administered in step k) is *Sutterella*.

9. The method of claim 1, wherein the probiotic administered in step k) is *Faecalibacterium*.

10. The method of claim 1, wherein the best matching donor is the individual prior to infection.

11. The method of claim 1, wherein the best matching donor is a family member of the individual.

12. The method of claim 1, wherein the step of preparing the DNA library of the microbiome of the infected individual comprises using shotgun sequencing.

13. The method of claim 1, wherein the step of preparing the DNA library of the microbiome of the infected individual comprises using next generation sequencing.

14. The method of claim 1 further comprising administering an antibiotic to the infected individual prior to the step of administering the probiotic.

15. The method of claim 1 further comprising administering an antiparastic to the infected individual prior to the step of administering the probiotic.

16. The method of claim 1, further comprising administering atropine after the step of administering the probiotic.

17. The method of claim 1, further comprising administering diphenoxylate after the step of administering the probiotic.

* * * * *